United States Patent

Suzuki et al.

[11] Patent Number: 5,754,621
[45] Date of Patent: May 19, 1998

[54] X-RAY INSPECTION METHOD AND APPARATUS, PREPREG INSPECTING METHOD, AND METHOD FOR FABRICATING MULTI-LAYER PRINTED CIRCUIT BOARD

[75] Inventors: Yoko Suzuki, Yokohama; Hideaki Doi, Tokyo; Yasuhiko Hara, Machida; Koichi Karasaki, Hadano; Tadashi Iida, Isehara, all of Japan

[73] Assignee: Hitachi, Ltd., Tokyo, Japan

[21] Appl. No.: 769,218

[22] Filed: Dec. 18, 1996

Related U.S. Application Data

[63] Continuation of Ser. No. 212,763, Mar. 15, 1994, abandoned.

[30] Foreign Application Priority Data

Mar. 15, 1993 [JP] Japan ...................... 5-053489
May 25, 1993 [JP] Japan ...................... 5-122345

[51] Int. Cl.$^6$ ...................... G01N 23/04
[52] U.S. Cl. ...................... 378/57; 378/51; 378/58
[58] Field of Search ...................... 378/51, 55, 57, 378/58, 62

[56] References Cited

U.S. PATENT DOCUMENTS 4,910,757 3/1990 Kiyasu et al. ...................... 378/58
5,097,492 3/1992 Baker et al. ...................... 378/58

FOREIGN PATENT DOCUMENTS

| 55-42640 | 3/1980 | Japan. |
| 61-61003 | 3/1986 | Japan. |
| 1-204648 | 8/1989 | Japan. |
| 4-310813 | 11/1992 | Japan. |
| 5-21548 | 1/1993 | Japan. |

OTHER PUBLICATIONS

"International Tables for X-ray Crystallography", 1968 pp. 59–65.

*Primary Examiner*—Don Wong
*Attorney, Agent, or Firm*—Antonelli, Terry, Stout, & Kraus, LLP

[57] ABSTRACT

An X-ray inspection apparatus and method in which an object to be inspected is irradiated with characteristic X-rays containing at least one wavelength which affords a high X-ray absorbance in the object to be inspected. A transmitted X-ray image which has passed through the object to be inspected is detected, and the object to be inspected is inspected on the basis of the transmitted X-ray image. The method and apparatus are utilized to fabricate a multi-layer printed circuit board.

46 Claims, 15 Drawing Sheets

FIG. 9(a)
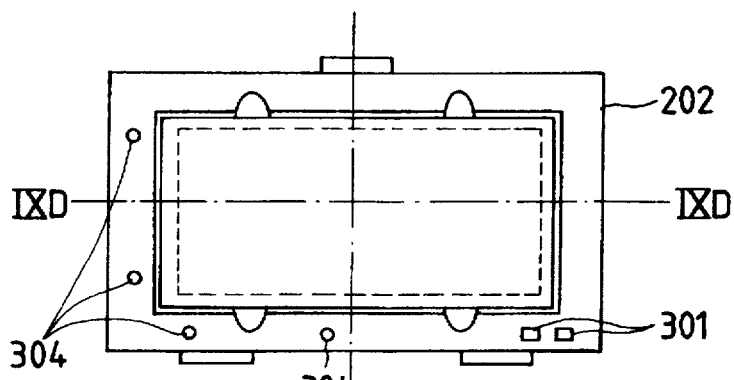
FIG. 9(b)
FIG. 9(c)
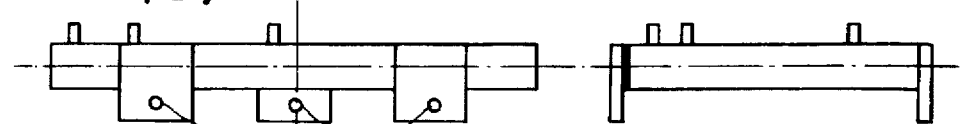
FIG. 9(d)
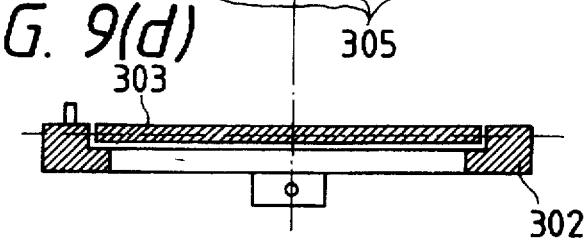
FIG. 10(a)
FIG. 10(b)
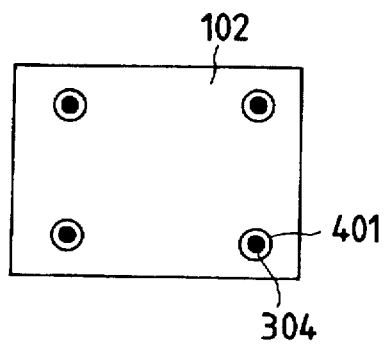
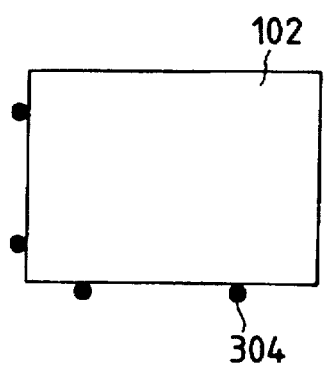

FIG. 25(a)　　　　　FIG. 25(b)
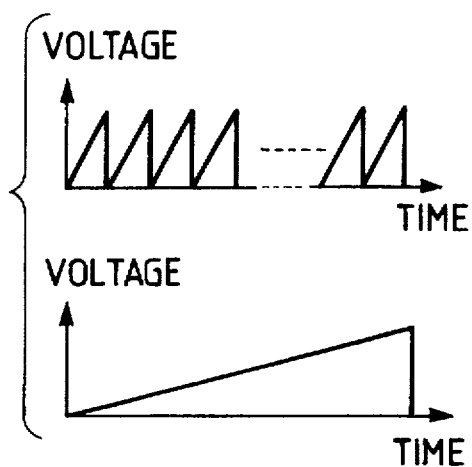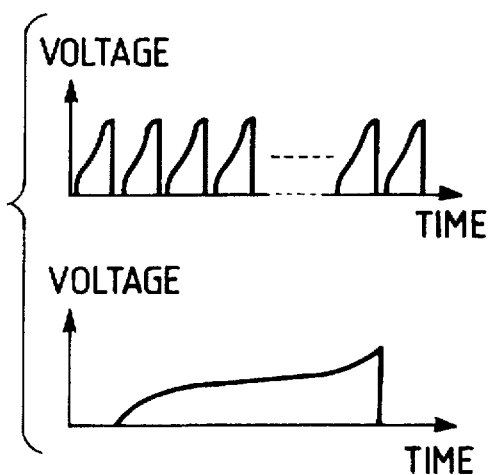
FIG. 26
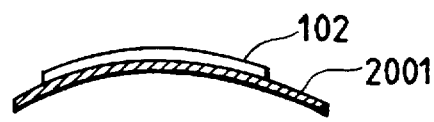
FIG. 27
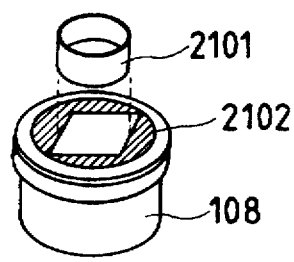

X-RAY INSPECTION METHOD AND APPARATUS, PREPREG INSPECTING METHOD, AND METHOD FOR FABRICATING MULTI-LAYER PRINTED CIRCUIT BOARD

This application is a continuation application of Ser. No. 08/212,763, filed Mar. 15, 1994, now abandoned.

BACKGROUND OF THE INVENTION

The present invention relates to an X-ray inspection method and apparatus for inspecting an object to be inspected on the basis of a transmitted X-ray image obtained from the object to be inspected. More particularly, the invention is concerned with an X-ray inspection method and apparatus wherein X-rays containing many wavelengths which afford a high X-ray absorbance in an object to be inspected are radiated to the object to obtain a clear transmitted X-ray image and the object to be inspected is inspected with a high accuracy on the basis of the image thus obtained.

As a conventional X-ray generator there is known, for example, the X-ray generator described in Japanese Patent Application Laid Open Nos. 204648/89 and 42640/80, in which X-rays are radiated to an object to be inspected (e.g. test sample) and the X-rays which have passed through the object are detected by an X-ray detector.

According to the X-ray generator described in the above publications, however, no special consideration is given to generating X-rays of specific wavelengths according to an object to be inspected and radiating such X-rays to the object. In the prior art, continuous X-rays are generated bremsstrahlung upon radiation of an electron beam to a target, but the continuous X-rays are generated merely in terms of a spectral distribution having a certain width.

Generally, X-ray absorbance in an object to be inspected differs depending on the wavelength of X-ray and the X-ray absorbance for specific wavelengths of X-rays also differ depending on the material of the object to be inspected. In other words, in order to obtain a clear transmitted X-ray image from an object to be inspected, it is desirable that as X-rays to be radiated to the object there be used characteristic X-rays of wavelengths affording high X-ray absorbance in the material of the object to be inspected.

SUMMARY OF THE INVENTION

It is an object of the present invention to provide an X-ray inspection method and apparatus which permit a clear transmitted X-ray image to be obtained from an object to be inspected.

It is another object of the present invention to provide an X-ray inspection apparatus capable of inspecting with high reliability electrically conductive foreign matter mixed in or adhered to the interior or the surface of an insulating sheet which is called a prepreg and which is used in the fabrication of a multi-layer printed circuit board.

It is a further object of the present invention to provide a method for inspecting a prepreg to be used in the manufacture of a multi-layer printed circuit board of high quality which does not cause a short-circuit or a state akin to a short-circuit between wiring patterns, as well as a method for fabricating such multi-layer printed circuit board.

In order to achieve the above-mentioned objects, the present invention, in one aspect thereof, resides in an X-ray inspection method comprising radiating to an object to be inspected X-rays containing at least one wavelength which affords a high X-ray absorbance in the object to be inspected, detecting a transmitted X-ray image which has passed through the object to be inspected and inspecting the object to be inspected on the basis of the transmitted X-ray image.

In another aspect of the present invention, there is provided an X-ray inspection method comprising radiating to an object to be inspected characteristic X-rays containing a plurality of two or more wavelengths which afford a high X-ray absorbance in the object to be inspected, detecting a transmitted X-ray image which has passed through the object to be inspected and inspecting the object to be inspected on the basis of the transmitted X-ray image.

In a further aspect of the present invention, there is provided the feature of radiating, to a printed circuit board to be inspected, characteristic X-rays containing the wavelength of 0.04 nm–0.15 nm whose wavelength X-rays are absorbed well by circuit patterns made of Cu, Au or other metals, and inspecting the printed circuit board by detecting the penetrated X-ray image of the printed circuit board.

In another aspect of the present invention, there is provided the feature of radiating, to a printed circuit board to be inspected, whose patterns are made of Cu, Au or other metal, characteristic X-rays generated from a small area of a target having a dimension less than 20 μm by applying a focused electron beam onto the target which is made of Mo, Cu, Au, other metals or an alloy, and inspecting the printed circuit board by detecting the penetrated X-ray image of said printed circuit board.

In further aspect of the present invention, there is provided the feature of radiating, to an insulating material to be inspected, characteristic X-rays generated by applying a focused electron beam onto a target made of Mo, Cu, Au, other metals or an alloy, and inspecting small conductive particles in or on the insulating material by detecting the penetrated X-ray image of the insulating material.

In another aspect of the present invention, there is provided the feature of radiating, to an insulating material to be inspected, characteristic X-rays generated from a small area of a target having a dimension less than 20 μm by applying a focused electron beam onto the target which is made of Mo, Cu, Au, other metals or an alloy, and inspecting small conductive particles in or on the insulating material by detecting the penetrated X-ray image of the insulating material.

In a further aspect of the present invention, there is provided an X-ray inspection apparatus including a stage for resting an object to be inspected thereon and positioning the object; an X-ray source for radiating X-rays containing many wavelengths which afford a high X-ray absorbance in the object to be inspected to the object which has been positioned in place by the stage; an optical image conversion unit for detecting a transmitted X-ray image which has passed through the object to be inspected and converting it into an optical image; a photoelectric conversion unit for converting the optical image obtained by the optical image conversion unit into a transmitted X-ray image signal; an image processing unit for inspecting the object to be inspected on the basis of the transmitted X-ray image signal obtained by the photoelectric conversion unit; and a stage controller for controlling the movement of the stage.

In still further aspects of the present invention, there is provided in the above-noted X-ray inspection apparatus wherein the X-ray source is constituted by an X-ray tube, controllability of the tube voltage and the tube current.

Further, there is provided in the X-ray inspection apparatus, a target of the same material as that of the object to be inspected. Additionally, there is provided in the above-noted X-ray inspection apparatus, a target formed of an alloy of two or more kinds of metals.

In a still further aspect of the invention, there is provided an X-ray inspection apparatus including an X-ray source; an XY positioning stage for moving and positioning a test sample tray in X and Y axis directions; an X-ray photoconversion unit for radiating X-rays emitted from the X-ray source to the test sample which has been positioned in place by the XY positioning stage, detecting a transmitted X-ray image which has passed through the test sample and converting it into an optical image; a photoelectric conversion unit for receiving the optical image detected by the X-ray photoconversion means and detecting it as a transmitted light/shade X-ray image signal; a noise eliminating unit for eliminating a noise component from the transmitted light/shade image signal obtained by the photoelectric conversion unit; a level conversion unit for converting the level of the transmitted light/shade X-ray image signal after noise elimination by the noise eliminating unit into a signal level proportional to the thickness of the test sample; and a level correction unit for correcting a change in detected signal level of the transmitted light/shade X-ray image signal after conversion by the level conversion unit, wherein foreign matter mixed into the test sample and foreign matter adhered to the surface of the test sample are inspected on the basis of the transmitted light/shade X-ray image signal after correction by the level correction unit.

In yet another aspect of the invention, there is provided the aforementioned X-ray inspection apparatus an X-ray source constructed so as to radiate an electron beam or the like to a target convergedly in a very small area of the target and to cause X-rays to be generated from the very small area of the target.

In a still further aspect of the invention, there is provided in the aforementioned X-ray inspection apparatus an imaging magnification control unit for controlling an imaging magnification of the transmitted X-ray image detected by the X-ray photoconversion unit. Also, there is provided a conveyance unit for carrying a test sample tray of the test sample in and out between an auxiliary stage disposed outside a protective cabin and the XY positioning stage through a window capable of being opened and closed and formed in the protective cabin.

Additionally, there is provided an X-ray measuring unit for measuring the intensity of X-rays emitted from the X-ray source, wherein the detected signal level is corrected by the level correction unit in accordance with the intensity of X-rays measured by the X-ray measuring unit. Further, there is provided an X-ray measuring unit for measuring the intensity of X-rays emitted from the X-ray source and a control unit for controlling the X-rays emitted from the X-ray source in accordance with the intensity of X-rays measured by the X-ray measuring unit. Also, there is provided a display unit for displaying the transmitted light/shade X-ray image signal after correction by the level correction unit.

In a still further aspect of the invention, there is provided an X-ray inspection apparatus including an auxiliary stage disposed outside of a protective cabinet; an XY positioning stage for moving and positioning a test sample tray in X and Y axis directions; a conveyance unit for carrying the test sample tray in and out between the auxiliary stage and the XY positioning stage through a window formed in the protective cabinet and capable of being opened and closed; an X-ray source constructed so as to radiate an electron beam or the like to a target convergedly in a very small area of the target and to cause X-rays to be generated from the very small area; and a sensitizing unit for picking up and sensitizing onto a film, a transmitted X-ray image which has passed through the test sample irradiated with X-rays from the X-ray source and positioned in place by the XY positioning stage, to obtain an X-ray transmitted image, wherein foreign matter mixed into the test sample and foreign matter adhered to the surface of the test sample are inspected by the sensitizing unit.

In a still further aspect of the invention, there is provided a method for inspecting a prepreg, comprising radiating X-rays to the prepreg and checking whether a specified electroconductive foreign matter is mixed in the interior of the prepreg or adhered to the surface of the prepreg on the basis of a transmitted X-ray light/shade image which has passed through the prepreg.

In a still further aspect of the invention, there is provided a method for fabricating a multi-layer printed circuit board, comprising radiating X-rays to a prepreg, checking whether a specified electroconductive foreign matter is mixed in the interior of the prepreg or adhered to the surface of the prepreg on the basis of a transmitted X-ray light/shade image which has passed through the prepreg, then providing a prepreg free of the specified electroconductive foreign matter mixed in or adhered to the interior or the surface of the prepreg, and laminating and heating the provided prepreg and a printed circuit board having wiring patterns on an insulating material.

In inspecting an object to be inspected, using X-rays, if the X-rays contain many wavelengths which afford a high X-ray absorbance in the material of the object to be inspected and are radiated to the object in state including the object, there can be obtained a transmitted X-ray image as a clear image. By detecting such transmitted X-ray image and subjecting it to image processing, the object to be inspected can be inspected with a high accuracy.

On the other hand, a multi-layer printed circuit board or the like used in the fabrication of an electric circuitry is manufactured by forming wiring patterns (circuit patterns) on the surface of an insulating sheet which is called a prepreg, using an electrically conductive material such as copper, to provide a wiring pattern base, the prepreg being prepared by impregnating a mesh-like woven fabric sheet of glass fiber with an insulating material such as polyimide, and then laminating a large number of such wiring pattern bases through the insulating sheet of the prepreg. However, if an electrically conductive metallic foreign matter is mixed in or adhered to the interior or the surface of the insulating sheet, there will occur a short-circuit or a state akin to short-circuit between wiring patterns, so it is necessary to inspect it and eliminate any defect. In order to ensure reliability over a long period after the fabrication of such multi-layer printed circuit board, even if such electroconductive metallic foreign matter is not larger than several ten μm, it is necessary to detect it and prevent deterioration of insulation characteristics caused by migration for example of the wiring pattern formed of copper or any other electroconductive material. In view of this point and taking note of the fact that the insulating sheet which is called a prepreg is constituted by a material of a relatively low molecular weight and high in X-ray transmittance and that metals causing problems as electrically conductive metallic foreign matters are large in molecular weight and relatively low in X-ray transmittance, such as Fe, Mo and W, the present invention permits inspection of a very small electroconductive metallic foreign matter mixed in or adhered to the interior or the surface of the insulating sheet of prepreg. at a high reliability on the basis of an X-ray transmitted image. According to the present invention. therefore. only a specified value or less of such very small, electroconductive metallic foreign matter may be present in the interior or on the surface of the insulating sheet. Thus, by laminating a large number of the foregoing wiring pattern bases through the insulating sheet free of such very small, electroconductive metallic foreign matter, there can be obtained a multi-layer printed circuit board which can ensure the reliability of insulation characteristics over a long period.

These and other objects, features, and advantages of the present invention will become more apparent from the following description when taken in conjunction with the accompanying drawings which show, for purposes of illustration only, several embodiments of the present invention.

BRIEF DESCRIPTION OF THE DRAWINGS

FIGS. 9(a)–9(d) show an example of a test sample holding mechanism used in the apparatus in top, front, side and cross-sectional views, respectively;

FIGS. 10(a) and 10(b) are views showing an example of a positioning mechanism used in the apparatus;

FIGS. 25(a) and 25(b) are explanatory diagrams showing an example of a photoelectric converter driving method according to the invention;

FIG. 26 is an explanatory view showing an example of a test sample holding method according to the invention;

FIG. 27 is an explanatory view showing an example of an image improving method according to the invention.

DESCRIPTION OF THE PREFERRED EMBODIMENTS

Figure 1:
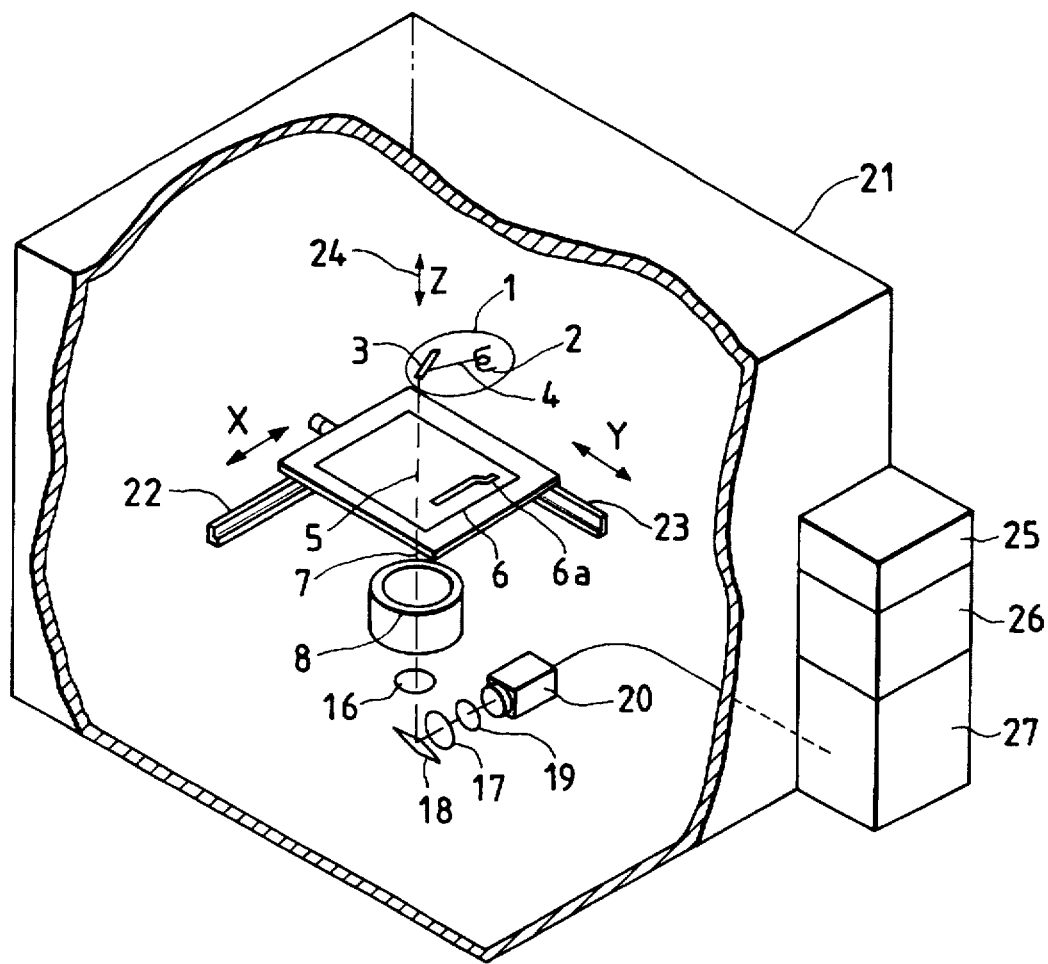
FIG. 1 is a view showing a schematic construction of an X-ray inspection apparatus according to an embodiment of the present invention.

Referring now to the drawings wherein like reference numerals are utilized to designate like parts throughout the several view, there is shown in FIGS. 1 to 6 an X-ray inspection apparatus according to an embodiment of the present invention wherein FIG. 1 illustrates a schematic construction of the X-ray inspection apparatus. In this embodiment, an object 6 to be inspected is assumed to be one having a circuit pattern 6a formed on the surface thereof, e.g., a printed circuit board, and X-rays emitted from an X-ray tube 1, are radiated thereto. In the X-ray tube 1, there is provided a target 3 of a material capable of generating a characteristic X-ray of a wavelength which affords a high X-ray absorbance in the circuit pattern 6a. When an electron beam 4 of a tube voltage not smaller than a value determined by the material of the target 3 is radiated to the target 3 from a cathode 2, an X-ray having a wavelength peculiar to the material of the target 3, namely a characteristic X-ray, is generated from the target and it is radiated to the object 6 to be inspected. The intensity of this characteristic X-ray is several times as high as continuous X-rays and the width of its wavelength distribution is very narrow. In this case, a tube voltage and a tube current in the X-ray tube 1 are set to optimum values by an X-ray generation controller 26 disposed outside of a cabinet 21. Where the tube voltage and current are set to optimum values so that the value of the tube voltage is maintained at a value not smaller than a value which permits generation of a characteristic X-ray from the target 3, and the value of tube current permits the generation of a characteristic X-ray having an intensity suitable for detection, there can be generated a specific X-ray having a desired intensity from the X-ray tube 1 which is radiated to the object 6 to be inspected.

Figure 2:
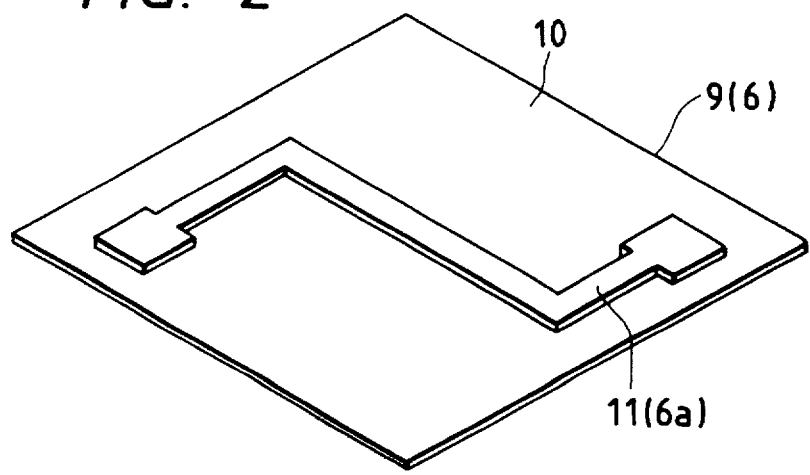
FIG. 2 is a view showing a printed circuit board as an object to be inspected.

FIG. 2 illustrates a printed circuit board as the object 6 to be inspected. As shown therein, the printed circuit board 9(c)

comprises a base 10 and various circuit patterns 11(6a) formed on the surface of the base. The material of the circuit patterns 11(a) is generally a metal and that of the base 10 is an organic material in many cases. Referring again to FIG. 1, assuming that the material of the circuit patterns 11(a) is copper and that of the base 10 is an organic material, when the characteristic X-ray emitted from the X-ray tube 1 is radiated to the printed circuit board 9, a portion of the X-ray is absorbed in the circuit patterns 11 and the remaining portion thereof passes through the circuit patterns. On the other hand, in the base 10, since the characteristic X-ray transmittance thereof is higher than that of copper, most of the characteristic X-ray radiated to the base 10 passes as it is through the base. The transmitted X-ray, indicated at 7 in FIG. 1, which has thus passed through the printed circuit board 9 is converted into an optical image by means of an image intensifier 8. Further, this optical image is detected as an image by a camera 20 through a lens 16, mirror 18, lens 17 and shutter 19, and the image thus detected is subjected to a predetermined image processing by means of an image processor 27, whereby the presence or absence of a defect (e.g. a short-circuit or disconnection) on the circuit patterns 11 (6a) is checked. In the image intensifier 8, an optical image is obtained from the transmitted X-ray 7, in which the image portion corresponding to the circuit patterns 11 (6a) is a dark portion and the image portion corresponding to the base 10 is a light portion. The printed circuit board 9 as the object 6 to be inspected is moved as desired in X and Y directions in a positioned and rested state on X stage 22 and Y stage 23, while the X-ray tube 1 itself is moved as desired in a Z direction 24 by means of a Z stage (not shown). Alternatively, the position of the X-ray tube 1 in the Z direction 24 may be fixed, and instead, the object 6 to be inspected may be moved in the Z direction by means of the Z stage. For controlling the movement of these X, Y and Z stages there is provided an XYZ stage controller 25.

Figure 3:
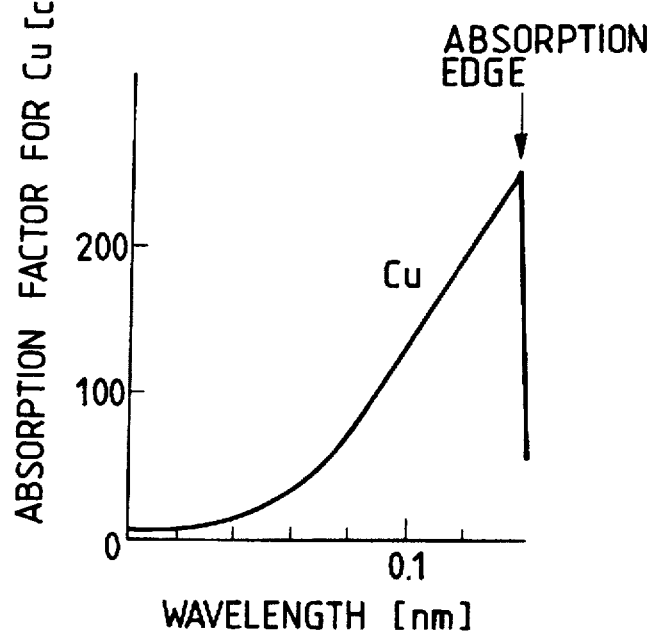
FIG. 3 is a diagram showing an absorption factor for copper relative to the wavelength of radiated X-rays.

The X-ray absorbance of copper Cu which is the material of the circuit patterns 11 differs depending on the wavelength of radiated X-ray. FIG. 3 shows mass declining coefficients or the absorption factor for copper, Cu, relative to radiated X-ray wavelengths. By using as target 3, a material capable of generating a characteristic X-ray of a wavelength corresponding to a large mass declining coefficient, namely a wavelength which affords a high X-ray absorbance, there can be detected an image corresponding to the circuit patterns 11 more clearly. According to the generation mechanism of a characteristic X-ray, as well known, when an inner shell electron of an atom, e.g. an electron of K shell, becomes null and a shell electron falls into that vacant place from an outer shell (e.g. L shell), an X-ray is generated using as energy an energy difference between both levels. The wavelength of a characteristic X-ray in the K series of Cu is about 0.16 nm, but this is at an absorption edge, that is, corresponds to an X-ray wavelength affording a high X-ray absorbance. In other words, a peak of X-ray absorbance in Cu appears at a wavelength of about 0.16 nm, and the shorter the wavelength, the lower the X-ray absorbance. As to metals other than Cu, the wavelength of a characteristic X-ray in the K series of tungsten W is about 0.02 nm and that of molybdenum is about 0.07 nm.

Figure 4:
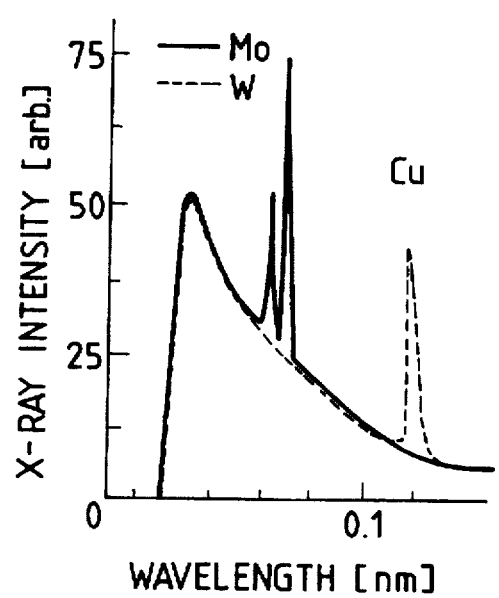
FIG. 4 is a diagram showing wavelength-generated X-ray intensity characteristics of Mo and W at an X-ray tube voltage set at 60 kV.

FIG. 4 illustrates wavelength-generated X-ray intensity characteristics with respect to molybdenum Mo and tungsten W at a tube voltage in the X-ray tube set at 60 kV. From the figure, it is seen that in the case where the material of the circuit pattern 11 is Cu, the characteristic X-ray of W as the target 3 doesn't exist in the range of large X-ray absorbance in Cu. However, the use of Mo as the target 3 permits the generation of X-ray having a wavelength closer to the wavelength which affords a high X-ray absorbance in copper. In other words, in the case where the circuit patterns 11 are formed of Cu, the use of Mo target 3 is more desirable than the use of W target 3 in detecting an image of the circuit patterns 11 more clearly. In the case of using Mo as the material of the target 3, it is necessary that the tube voltage be set at a value not smaller than 28 kV which is a value permitting the generation of a characteristic X-ray in the K series. It is also necessary that a tube current required for generating X-ray having an intensity suitable for image detection, namely, a tube current required for obtaining a transmitted x-ray having an intensity neither short nor in excess in the quantity of light relative to the image intensifier 8, be set to an optimum value. More specifically, the requirements can be satisfied, for example, by setting tube voltage and current at 60 kV and 20 mA, respectively, and making adjustment to generate a characteristic X-ray having a wavelength of about 0.07 µm. The tube voltage and current thus set may be set again to optimum values at every change in conditions of the object 6 to be inspected, stage, etc. More particularly, the value of tube current can be newly set to an optimum value by a feedback control based on the level of a detected image signal or that of a detected transmitted X-ray signal provided from a transmitted X-ray sensor disposed separately.

In the above embodiment Mo, is used as the material of the target 3 in the case where the material of the circuit patterns 11 is Cu. In this case, the wavelength of the X-ray affording a high absorbance in Cu is also the wavelength at the absorption edge of Cu, which wavelength is equal to that of the characteristic X-ray of Cu. Therefore, if Cu is used as the material of the target 3 and X-rays 5 containing the characteristic X-ray of Cu are radiated to the printed circuit board 9, the amount of X-ray absorbed in Cu increases, so that the optical image obtained from the image intensifier 8 is clearer in which the image portion corresponding to the circuit patterns 11 is darker. By inspecting a clearer image corresponding to the circuit patterns 11, it is made possible to inspect finer defects on the circuit patterns. Although in the above embodiment the material of the circuit patterns 11 is assumed to be Cu, in the case where gold, Au, is used as the pattern material such that circuit patterns reside in a LSI package, for example, the use of Au as the material of the target 3 makes it possible to obtain the same effect as that obtained in the use of Cu as the material of the circuit patterns 11. Moreover, although in the above embodiment, the object to be inspected is only the circuit patterns 11, it is also possible to detect metals contained as foreign matter in the base 10. Since a metallic foreign matter is higher in X-ray absorbance than the base 10, if X-rays 5 containing a characteristic X-ray of a wavelength affording a high X-ray absorbance in the metallic foreign matter as the object to be inspected are radiated to the base 10, the metallic foreign matter can be detected in a dark state of its image portion. Further, although in the above embodiment, the target 3 is constituted by one kind of metal, it may be constituted by an alloy of two or more kinds of metals or a mixture of those metals as the case may be. For example, in the case where Cu is used as the material of the circuit patterns 11, if Cu or an alloy of Mo and Cu is used as the material of the target 3, there can be obtained a clearer X-ray transmitted image. The object 6 to be inspected is not limited to the printed circuit board 9. For example, it may be a soldered portion of electronic circuit components.

In the above embodiment, the X-rays 5 from the X-ray tube 1 are radiated directly to the object 6 to be inspected.

Figure 5:
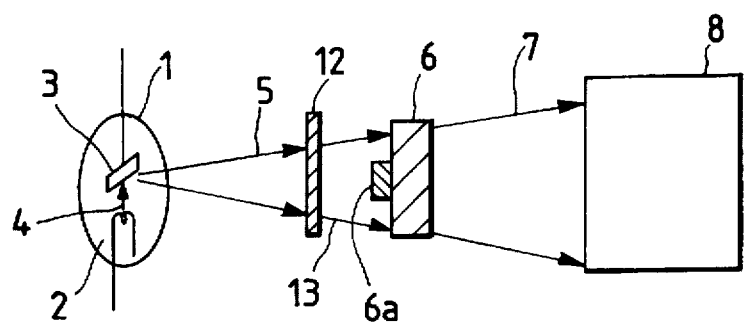
FIG. 5 is a view showing a basic construction of the X-ray inspection apparatus when extracting only X-rays of a specific wavelength through a filter and radiating such X-rays to the object to be inspected.

As shown in FIG. 5, however, the X-rays 5 may be radiated as filter transmitted X-rays 13 through a filter 12 to the object 6 to be inspected. An X-ray of a wavelength affording a low X-ray absorbance in the object 6 to be inspected corresponds to an X-ray of a wavelength affording a high X-ray absorbance in the filter 12, so that an X-ray of a wavelength affording a high X-ray absorbance in the object 6 is mainly radiated to the object, whereby there is obtained a clearer X-ray transmitted image.

Figure 6A:
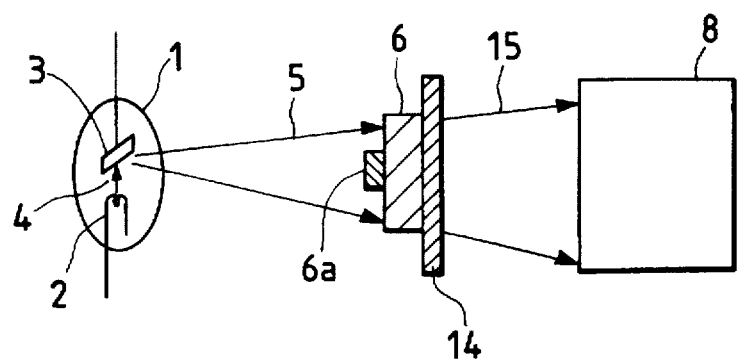
FIGS. 6(a) and 6(b) are views showing a basic construction of the X-ray inspection apparatus when radiating X-rays to the object to be inspected and also taking an object support member and the like into consideration with FIG. 6(b) showing a small area of a target.
Figure 6B:
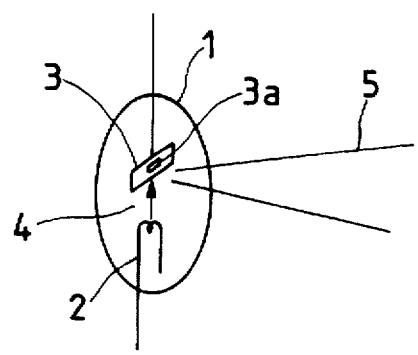

Although no special consideration is given to an object support member for supporting the object to be inspected, which support member is typified by an XYZ stage, in the case where the X-rays 5 from the X-ray tube 1 are radiated to the object 6 to be inspected in a supported state of the object on a support member 14, as shown in FIG. 6(a), X-rays 15 which have passed through the object 6 to be inspected and the object support member 14 are detected by the image intensifier 8. In this connection, if an X-ray of an optimum wavelength is selected in view of the X-ray absorbance in the entire portion also including a portion other than the object 6 to be inspected such as the object support member 14, there can be obtained a clearer transmitted X-ray image. More particularly, as shown in FIG. 6(b) the characteristic X-rays containing a wavelength of 0.04 nm to 0.15 nm are generated from a very small area 3a of the target 3 having a dimension of 20 μm or less by radiating a convergent electron beam into area 3a of the target 3 formed, for example, of Mo, Cu, or Au, or an alloy thereof.

Figure 7:
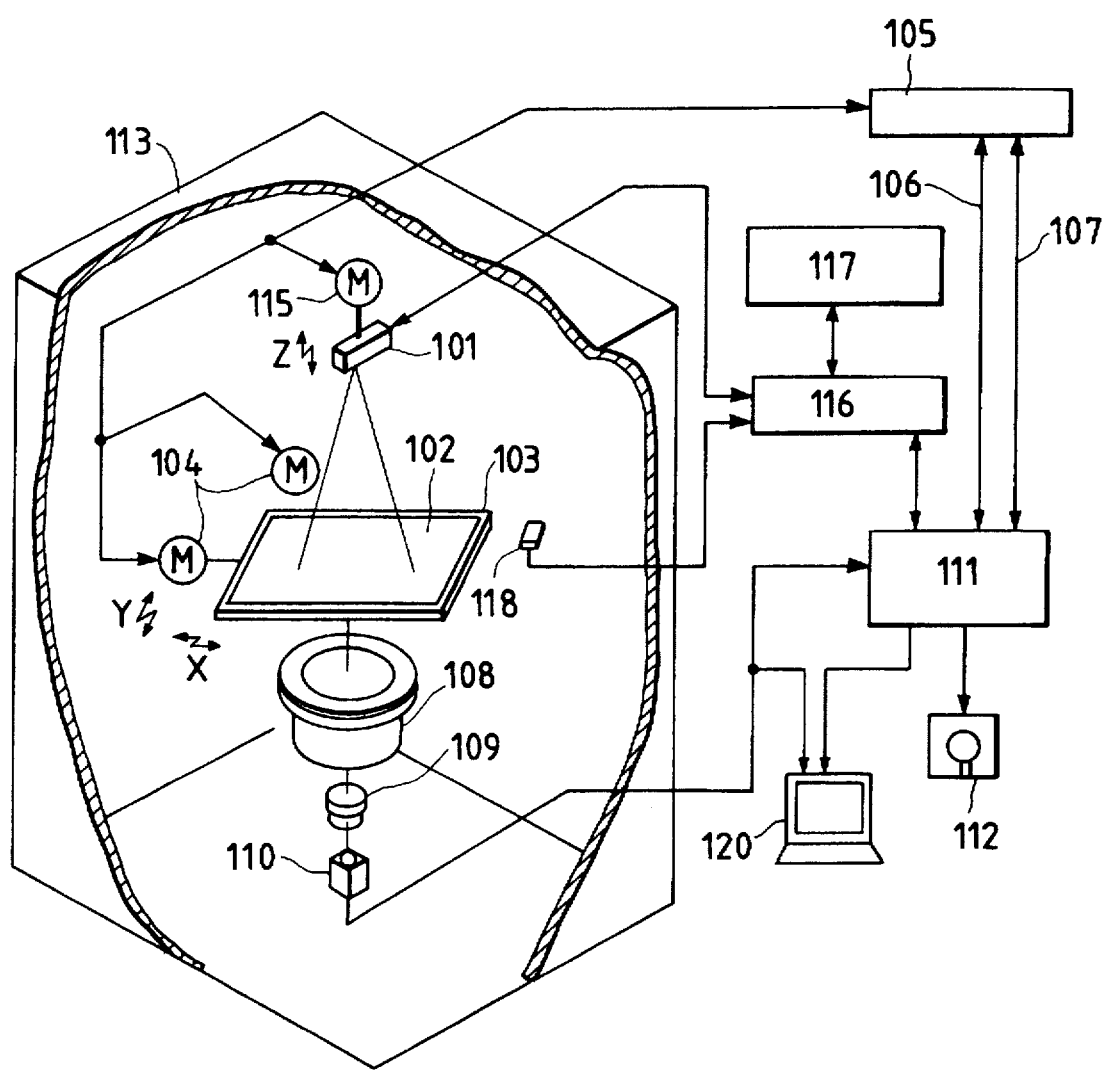
FIG. 7 is a block diagram showing a construction of an X-ray inspection apparatus according to another embodiment of the present invention.

FIG. 7 is a block diagram showing a construction of a foreign matter inspecting apparatus according to another embodiment of the invention and the following description is directed to where inspection is to be made with respect to an electrically conductive, very small, metallic foreign matter such as Fe, Mo or W not larger than several 10 μm and present in a mixed or adhered state in the interior or on the surface of an insulating sheet such as a prepreg which is used in a multi-layer printed circuit board.

In FIG. 7, there is shown an X-ray source 101 which emits an electron beam or the like to a target convergedly in a very small area and which can be regarded as a point source; a test sample 102 such as an insulating sheet, for example; an XY positioning stage mechanism 103 for moving and positioning the test sample 102 at least in X and Y axis directions while holding the test sample; motors 104 for driving the XY positioning stage mechanism 103; a motor 115 for driving a Z stage which moves the X-ray source 101 in a Z axis direction; a stage controller 105 which makes displacement (coordinates) measurement using a displacement measuring device and controls the movement of the XY positioning stage mechanism 103 and that of the Z stage at an arbitrary timing; stage control signal 106; coordinate data 107 obtained by the displacement measuring device; an X-ray photoconverter 108 such as an image intensifier; a detecting optical system 109; a photoelectric converter 110, e.g. television camera; a signal processing circuit 111; a test result 112; a protective cabinet 113; and an X-ray controller 116 which controls the X-ray source 101 on the basis of the X-ray control data 117 and the intensity of X-ray emitted from the X-ray source and measured by an X-ray measuring device 118 and which corrects a change in the quantity of light in the signal processing circuit 111.

The X-ray controller 116 shown in FIG. 7 is for adjusting the voltage and current to be applied to the X-ray source 101. It controls the X-ray source 101 so as to emit X-rays only when an X-ray shielding window which will be described later is closed after conveyance of the test sample 102 such as an insulating sheet into the protective cabinet 113. Further, on the basis of the X-ray quantity control data 117, the voltage and current to be applied to the X-ray source 101 are adjusted so as to radiate optimum X-rays to the test sample 102. In this case, by disposing the X-ray dose measuring device 118 in the vicinity of the X-ray photoconverter 108 and adjusting the current so that the X-ray dose detected by the X-ray dose measuring device 118 is a desired value, there can be obtained a desired value of X-rays radiated to the test sample 102, so that a constant X-ray transmitted image is obtained from the test sample and thus it is possible to effect the inspection stably.

By moving the Z stage which carries the X-ray source 101 in the Z axis direction, using the motor 115 shown in FIG. 7, it is possible to change as desired a magnification which is determined by both the distance between the X-ray source and the test sample and the distance between the X-ray source and the X-ray photoconverter. Consequently, it is possible to change the magnification according to the test sample 102 or make a visual check using a monitor 120 on the basis of a transmitted X-ray image signal obtained from the photoelectric converter 110 while changing magnification after the end of the inspection. Usually, the input-output side magnification in the X-ray photoconverter 108 can be changed by changing light condensing conditions in the interior electron lens, but in combination with the movement of the X-ray source 101 in the Z axis direction, it is possible to set an optimum detecting magnification. Although in FIG. 7 the X-ray source 101 is moved in the Z axis direction by the motor 115, since the ratio between the X-ray source-test sample distance and the X-ray source-X-ray photoconverter distance defines the magnification, it is apparent that the above change of magnification may be achieved by movement of the test sample 102 in the Z axis direction or movement of the X-ray photoconverter 108 in the same direction or by a combined movement of both.

Figure 8A:
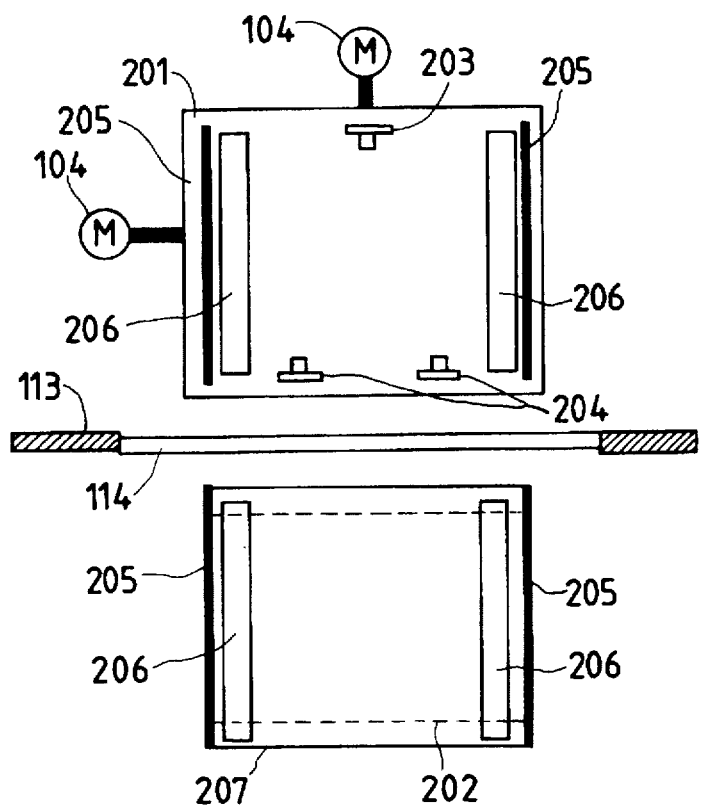
FIGS. 8(a)–8(c) show an example of a stage structure used in the apparatus in top, side and front views, respectively.
Figure 8B:
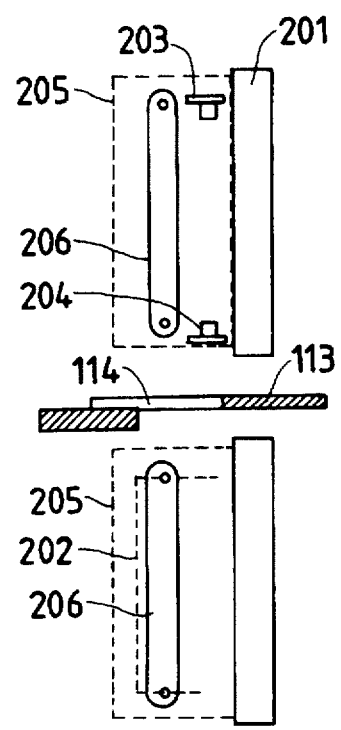
Figure 8C:
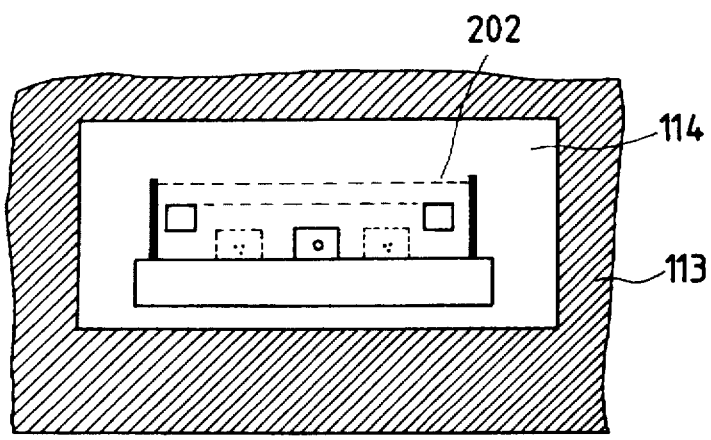

FIGS. 8(a)-(c) show an example of the XY positioning stage mechanism 103 in top, side and front views, respectively. According to this example, the XY positioning stage mechanism 103 comprises an XY stage 201 disposed within the protective cabinet 113 and adapted to move in the XY axis directions, a sample tray 202 for resting the test sample 102 thereon, conveyor belts 206 for carrying in and out the sample tray 202 along conveyance guides 205 and through the X-ray shielding window 114 which is opened and closed from the exterior of the protective cabinet 113, positioning pins 203 and 204 for positioning the sample tray 202 which has been carried in by the conveyor belts 206 onto the XY stage 201, an auxiliary stage 207 disposed outside the protective cabinet 113 for resting the sample tray 202 thereon, conveyance guides 205 disposed on the auxiliary stage 207 for guiding the sample tray 202, and conveyor belts 206 disposed on the auxiliary stage 207 for carrying the sample tray 202 into and out of the protective cabinet 113 through an X-ray shielding window 114. The X-ray shielding window 114 has an X-ray shielding movable plate provided in the cabinet 113.

FIGS. 9(a)-(d) show in top, front, side and cross-sectional views of an example of structure of the sample tray 202 which comprises a frame 302 having a groove for receiving a holding plate 303 therein. There is also provided guide pins 304 for positioning engagement with reference holes or plane formed on the test sample 102 side, and positioning holes 305 for fitting therein of the positioning pins 203 and 204 formed on the XY stage 201 and thereby positioning the sample tray 202. Conveyor belts 206 move the sample tray 202 between the XY stage 201 and an auxiliary stage 207 along conveyance guides 205 and through the X-ray shielding window 114. On the auxiliary stage 207, the test sample 102 is positioned in place by the guide pins 304 and put onto the holding plate 303, then moved, together with the sample tray 202, onto the XY stage 201 by the conveyor belts 206 and is positioned in place on the XY stage 201 by engagement of the positioning holes 305 formed in the frame 302 of the sample tray 202 with positioning pins 203 and 204 provided on the XY stage 201. The positioning pins 204 are movable and move upward to predetermined positions to position the sample tray 202 in place after the sample tray has been carried onto the XY stage 201. For carrying out the sample tray 202 from the XY stage 201, the positioning pins 204 are disengaged and moved downward.

By providing the frame 302 and the holding plate 303 as separate components, it is possible to select a material low in X-ray transmittance for the holding plate 303 and a material high in rigidity for the frame 302 and thereby possible to constitute a stage optimum for X-ray inspection. According to this construction, moreover, since the positioning of the stage (sample tray) 102 is performed by the frame 302, flaw and damage of the holding plate 303, which are apt to influence the results of inspection, can be repaired easily by replacement only of the holding plate and thus the maintenance is extremely easy. Further, in the case where plural test samples 102 are to be inspected, the most suitable holding plate 303 can be selected and used according to the material of each test sample 102.

It is apparent that the holding plate 303 is not necessary when the rigidity of the test sample 102 itself is high. In this case, by removing the holding plate 303, it is made possible to diminish the unnecessary attenuation of X-rays.

Since the test sample 102 can be set outside the protective cabinet 113 by using the auxiliary stage 207, the operability is improved, and by the radiation of X-rays in a closed state of the X-ray shielding window 114 at the time of inspection, an operator can be easily protected from X-rays which are harmful to the human body.

The test sample 102 is positioned in place outside the protective cabinet 113 by the guide pins 304 and is put on the sample tray 202. FIGS. 10(a) and 10(b) show examples of the test sample 102, in which FIG. 10(a) shows a test sample 102 having positioning guide holes 401 and FIG. 10(b) shows a test sample 102 not having such guide holes. In the example of FIG. 10(a), the guide holes 401 are used as consistent reference positions throughout the manufacturing process, so it is possible to make a consistent and accurate control for foreign matter coordinates detected from the transmitted X-ray image and it becomes possible to unify a defective coordinates control and a repair process as a combination with wiring pattern inspection results after the formation of wiring patterns, for example. In the example shown in FIG. 10(b), pretreatment for forming the guide holes is not necessary.

In both examples, a single or plural test samples 102 may be inspected at a time. The inspection time can be shortened by inspecting plural test samples at a time.

Figure 11A:
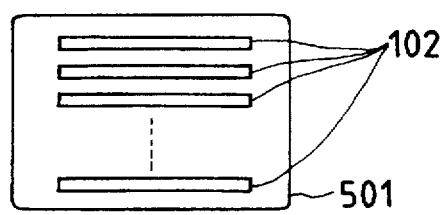
FIGS. 11(a)–11(d) are explanatory views of a test sample.
Figure 11B:
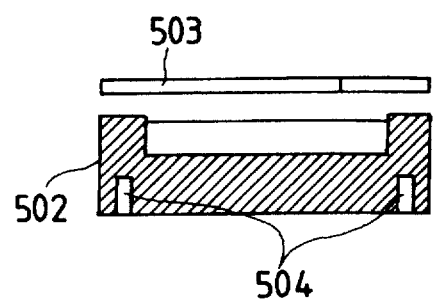
Figure 11C:
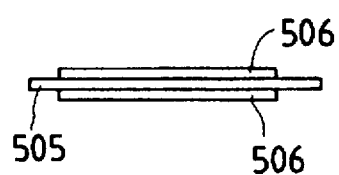
Figure 11D:
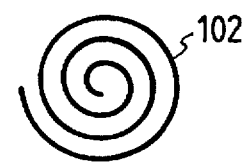

As shown in FIG. 11(a), it is also possible to inspect a single or plural test samples 102, e.g. a prepreg, in a contained state in a protective bag 501. This is advantageous in that the influence of adhered foreign matter can be eliminated during transport and storage of the test sample 102 after the preparation thereof. It is also possible to make inspection of powder or liquid by using a sample box 502, as shown in FIG. 11(b). Although guide holes 504 are formed in the example shown in FIG. 11(b), it is also possible to use the outer wall of the sample box 502 for positioning purpose as in the example shown in FIG. 10(b). According to the example shown in FIG. 11(b), the inspection of powder or liquid can be achieved in terms of accurate coordinates. It is apparent that the structure of the sample box 502 is not specially limited if only it can hold the test sample 102. It is optional whether a lid 503 is to be used or not. This depends on the test sample 102. The test sample 102 may be a so-called copper-clad laminate such as that shown in FIG. 11(c), which is used in the formation of wiring patterns and which comprises an insulating material 505 and a homogeneous electroconductive material 506, e.g. copper, laminated onto the surface of the insulating material. Further, the test sample 102 may be in the form of a roll, as shown in FIG. 11(d).

Figure 12A:
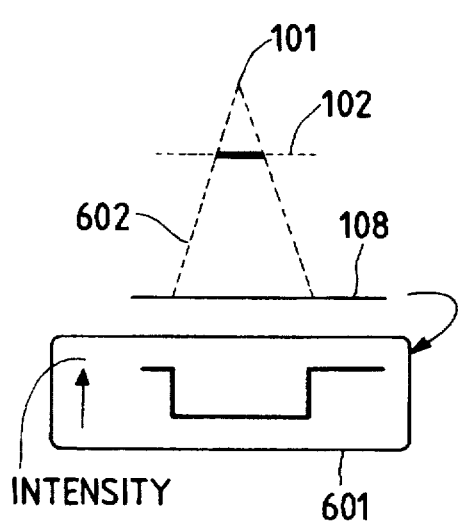
FIGS. 12(a) and 12(b) are explanatory views of the occurrence of blur in the use of X-rays.
Figure 12B:
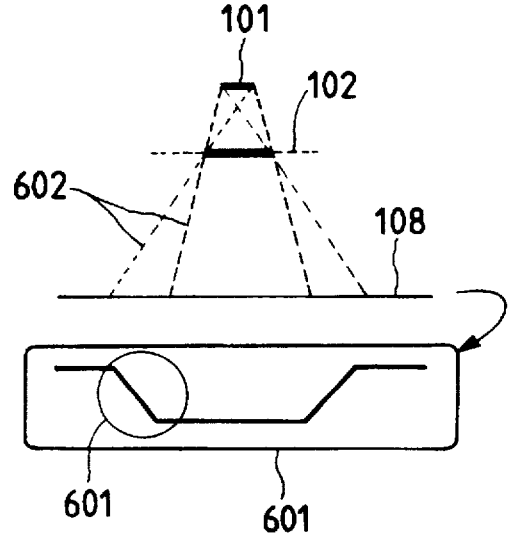

As shown in FIG. 7, the test sample 102 which has been set within the protective cabinet 113 is irradiated with X-rays and a transmitted X-ray image therefrom is converted into an optical light/shade image by the X-ray photoconverter 108. The magnification of the optical light/shade image is suitably changed by the detecting optical system 109, and after conversion into an electric signal in the photoelectric converter 110, very small, electroconductive, metallic foreign matters mixed in the interior and adhered to the surface of the test sample 102 are detected in the signal processing circuit 111 on the basis of a change in the electric signal. At this time, detection coordinates of the very small, electroconductive, metallic foreign matters are controlled by reference to coordinate data provided from the stage controller 105. If an X-ray source which generates a conical beam of X-rays is used as the X-ray source 101, the transmitted X-ray image of the test sample 102 obtained by the X-ray photoconverter 108 is magnified to a magnification which is determined by both the distance between the X-ray source and the test sample and the distance between the X-ray source and the X-ray photoconverter, so it is possible to effect an inspection which is independent of the coordinate resolutions of the X-ray photoconverter 108 and other elements. Further, if the X-ray source 101 is of the type in which electron beam or the like is radiated to a target convergedly in a very small area to generate X-rays 602, the source size can be regarded as a spot and, as shown in FIG. 12(a), it is possible to obtain a detected signal waveform 601 containing little deformation such as deterioration indicated at 601 which is generated at an edge portion of a very small metallic foreign matter such as Fe, Mo or W which is not larger than several ten μm as in FIG. 12(b). Such a signal which is slightly deteriorated permits a high-sensitivity detection of a very small metallic foreign matter.

Figure 13:
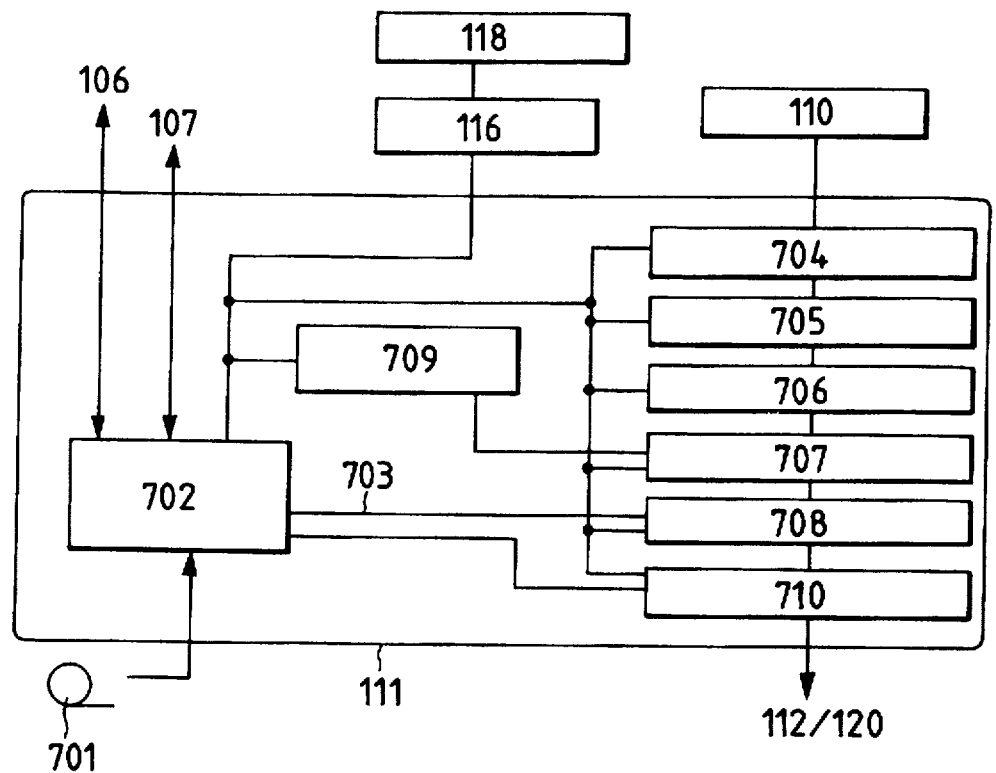
FIG. 13 is a block diagram showing an example of construction of a signal processing circuit used in the apparatus.

FIG. 13 shows an example of the signal processing circuit 111. The XY positioning stage mechanism 103 is moved stepwise or continuously by the motor 104 shown in FIG. 7. At this time, a stage control signal 106 can be generated on the basis of design information 701. For example, the design information 701 contains wiring information of the wiring (circuit) pattern base, namely, information indicating which portion of the test sample 102 is actually effective as circuit. Therefore, by moving the stage on the basis of the design information 701 so as to scan only the actually necessary portion in the manufacture of product, it is possible to shorten the inspection time and improve the product yield. Also contained as design information 701 are the size and thickness of the test sample 102 such as a prepreg, which are used in defining an inspection area or setting an imaging magnification.

Figure 14:
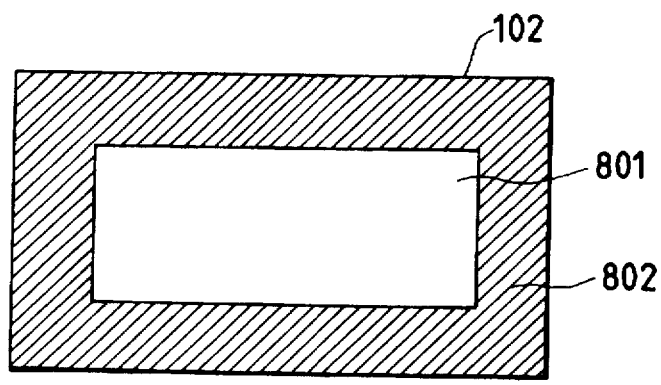
FIG. 14 is an explanatory view showing an example of an inspection area used in the apparatus.

If it is assumed that the test sample 102 is composed of a wiring pattern forming area 801 and a non-wiring pattern forming area 802, as shown in FIG. 14, since coordinate values which define these areas are found in the design information 701, it suffices to move the XY stage on the basis of such values so as to inspect only the wiring pattern forming area of the test sample 102 such as a prepreg (it is apparent that the inspection may be made in a divided manner).

An electric signal obtained by the photoelectric converter 110, which signal is proportional to the X-ray transmittance of the test sample 102, is improved in its quality by use of a noise eliminating circuit 704 utilizing image frame integration or a mean value or median filter, then is fed to a level converter 705 for the conversion of signal level, and then a level variation in a short period substantially corresponding to the photoelectric conversion storage time is corrected by a light quantity variation correcting circuit 706. Subsequently, shading which is generated in the X-ray photoconverter 108, the detecting optical system 109, etc. is corrected by a shading correction circuit 707. Correction data 709 is a reference data for the correction of shading which data is set before start of the inspection. In a decision circuit 708, a very small metallic foreign matter is detected on the basis of the signal corrected in the above correction circuit. At the same time, an inspection output 710 is produced by making reference to coordinate data 703 obtained from a coordinate control/signal control circuit 702. It is also possible to display the coordinate data of such very small metallic foreign matter on the monitor or display 120.

Figure 15:
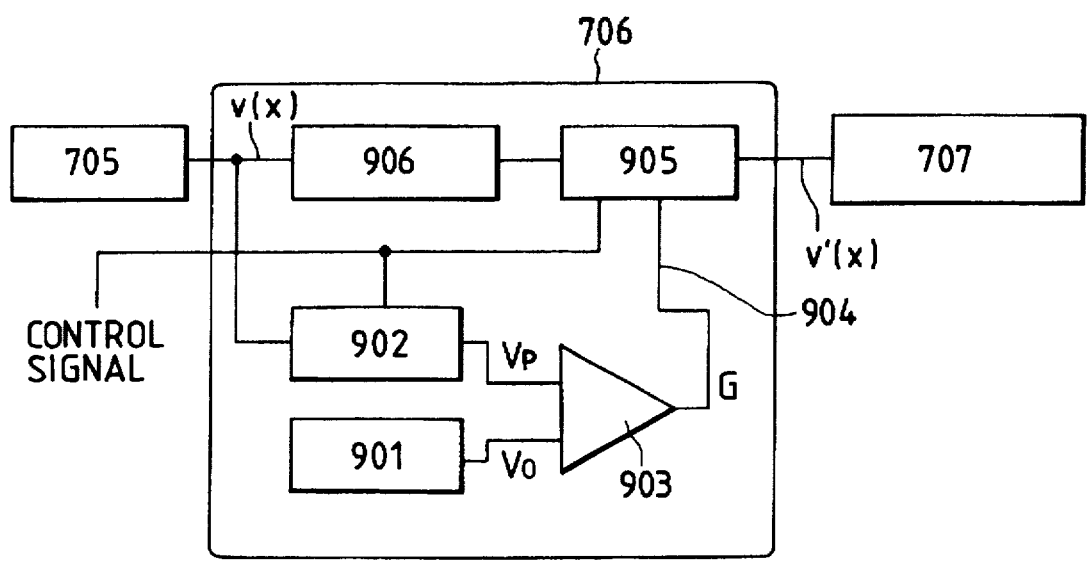
FIG. 15 is a block diagram showing an example of construction of a light quantity variation correcting circuit used in the apparatus.

FIG. 15 shows an example of the light quantity variation correcting circuit 706. A signal v(x) fed from the level converter 705 is inputted and stored into a frame memory 906. It is also inputted to a peak detecting circuit 902 receiving a control signal and a maximum value i n a detection frame is stored therein. When the scanning of one frame is over, an output VP of the peak detecting circuit 902 is compared with Vo set at a reference level 901 by means of a comparator 903. As a result, a gain G 904 (O<G<x, x being an arbitrary numerical value) is provided to an amplifier 905 as a gain for the reference value. Next, the detection signal v (x) stored temporarily in the frame memory 906 is converted into a signal v' (x) having a suitable amplification level by means of the amplifier 905, which signal is applied to the shading correction circuit 707 located in the next stage.

Figure 16A:
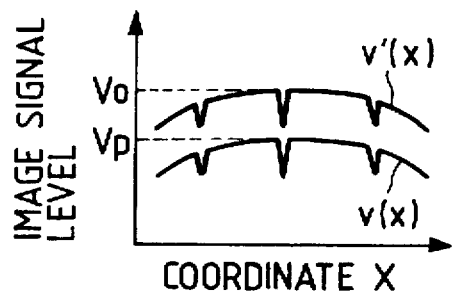
FIGS. 16(a)–16(d) are diagrams for explaining the function of the signal processing circuit.
Figure 16B:
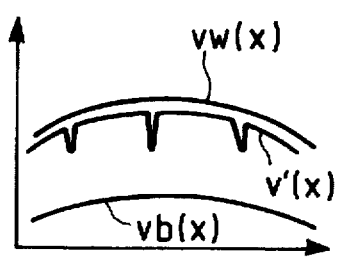

FIG. 16(a) shows an example of the signal v(x) inputted to the light quantity variation correcting circuit 706. In FIG. 16, v (x) represents an input signal whose level is low as a whole, v' (x) represents an input signal (a target value in the correction) which is in a normal state, and x represents a coordinate value. It is presumed that a variation of v' (x) is caused, for example, by a change in the X-ray generation efficiency induced by disturbance of electron beam at the time of generating X-rays. If the input signal is v (x) and a peak value thereof is Vp, a gain G is given, for example, by the following equation (Eq. 1), using the preset reference level Vo:

$$G = Vo/Vp \qquad \text{(Equation 1)}$$

Therefore, the signal v' (x) after the correction of light quantity variation is given by the following equation:

$$v'(x) = G \times v(x) \qquad \text{(Equation 2)}$$

According to this example, such a variation in the detected signal level as in FIG. 16(a) which is unavoidable in the utilization of X-rays can be corrected, thus making a stable inspection possible.

It is apparent that the gain G may be based on the intensity of X-rays measured by another X-ray sensor, e.g. X-ray measuring device 118, disposed near the X-ray photoconverter 108, without being based on the peak signal Vp obtained from the detection signal v(x). As an example, the result of the X-ray dose measurement made by the X-ray measuring device 118 shown in FIG. 7 may be used. In this case, it is apparent that a suitable delay circuit is disposed between the X-ray measuring device 118 and the amplifier 905 to take synchronism between detection signals. Since in this example, the gain G is controlled on the basis of the output Vp of the peak detecting circuit, it is possible to diminish noise-induced errors at the time of peak detection.

It is generally known that the detection signal level A based on X-rays lowers in proportion to the material and thickness index of the test sample (object to be inspected) and on the basis of the following equation (Equation 3). In the level converter 705, for example, there is performed a logarithmic transformation of signal in accordance with the following equation (Equation 4) to make correction so that the signal level is proportional to the thickness, t, of the test sample 102. This example is advantageous in that the sensitivity is independent of the thickness, t, of the test sample (object to be inspected). Further, by providing a plurality of bottoms ($\log_e \alpha$) in the logarithmic transformation and changing over from one to another, it is made possible to change sensitivity according to the thickness, t, of the test sample:

$$A = A_0 \exp(-\mu t) \qquad \text{(Equation 3)}$$

$$\begin{aligned}\log_\alpha A &= \log_\alpha A_0 + \log(-\mu t) \qquad \text{(Equation 4)}\\ &= \log_\alpha A_0 + (\log e \,(-\mu t))/(\log_e \alpha)\\ &= \log_\alpha A_0 + (-\mu t)/(\log_e \alpha)\end{aligned}$$

where $A_0$ represents the intensity of X-rays radiated to the test sample, $\mu$ represents a constant determined by the material of the test sample, and t represents the thickness of the test sample.

For example, the level converter 705 may be constituted by a look-up table. In this case, not only the logarithmic transformation but also any desired transformation can be made. Therefore, a change in the sensitivity characteristic of the system which is induced, for example at the time of replacement of the X-ray photoconverter 108, can be absorbed by change of the look-up table. According to this example, it is possible to easily effect the maintenance of the apparatus and adjustment at the time of fabrication of plural units.

Figure 16C:
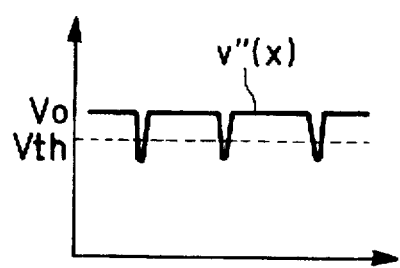

The shading correction circuit 707 corrects a change in the detection signal level within the detection field which is generated in the X-ray photoconverter 108 or the detecting optical system 109 for example. Reference data are needed in the correction, and an example for the realization thereof will now be described. Plural reference samples 301 different in thickness or according to the types of test samples, serving as a reference of detection level, are put on the sample tray 202. As such plural reference samples 301 there may be used, for example, the same material as the test sample 102 as a reference of light level and a material lower in X-ray transmittance than the test sample 102 as a reference of dark level. Alternatively, there may be provided plural reference samples 301 according to thicknesses of test samples. It is here assumed that the aforementioned light level Vw(x) and dark level Vb(x) are obtained as in FIG. 16(b), in which x represents coordinates. In the shading correction circuit 707, the following calculation for example is performed for each picture element, that is, for each x coordinates, to obtain a correction signal v" (x) given by the following equation (Equation 5), as shown in FIG. 16(c):

$$v''(x)=(v'(x)-vb(x))\times Vo/(vw(x)-vb(x))$$ (Equation 5)

This example is advantageous in that even if the constituent parts vary in sensitivity, etc. with the lapse of the working time of the apparatus, such variation can always be corrected. It is optional whether the reference sample 301 is to be provided only one or in a plural number. In the latter case, an optimum correction can be made according to conditions for the inspection.

Figure 16D:
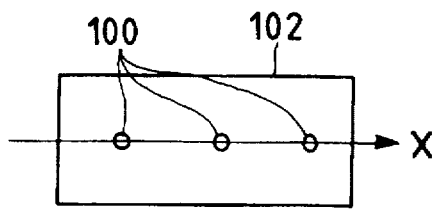

An example of the decision circuit 708 will now be described. An X-ray transmitted image of the test sample 102 is given as in FIG. 16(c) by the foregoing correction. FIG. 16(d) shows a test sample 102 which corresponds to FIG. 16(c). The transmitted image signal level of the test sample 102 is high, while that of the very small, electroconductive, metallic foreign matter 100 to be detected is low. Therefore, it suffices to binary-code the detection signal v"(x) using a suitable threshold value Vth, detect a detection level lower than Vth, namely, the dark portion of the detection signal, and output it as a fault output 710.

Figure 17A:
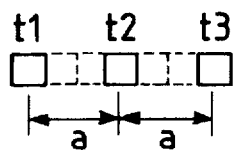
FIGS. 17(a)–17(c) are diagrams for explaining the function of a decision circuit used in the apparatus.
Figure 17B:
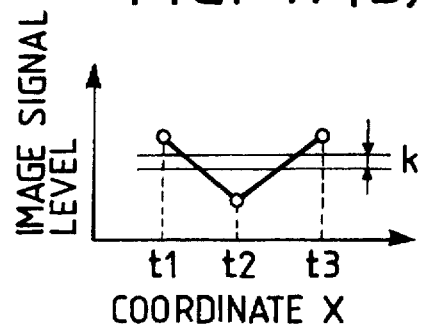

The fault output 710 may be detected using such an operator as shown in FIG. 17(a) which shows an example of operator in the x-axis direction. Reference picture elements t1, t2 and t3 are provided and the distance between t1 and t2 and that between t2 and t3 are each assumed to be a. In a foreign matter portion, as shown in FIG. 17(b), the conditions of the following equation (Equation 6) are valid, using k as an arbitrary decision value, so by detecting these conditions it is made possible to detect a foreign matter.

$$|t1-t2|>k \text{ and } |t2-t3|>k$$ (Equation 6)

Figure 17C:
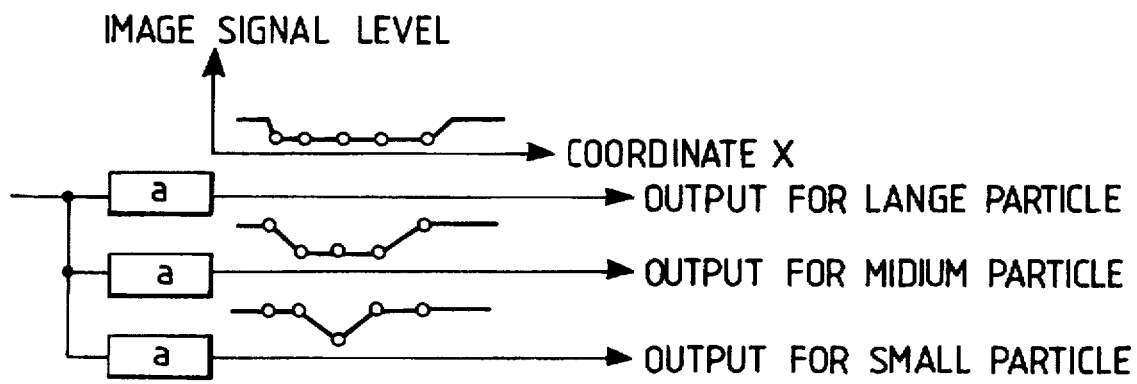

The number of the above reference picture elements and that of the above decision value are not limited to the above, but each may be a required plural number. There also may be provided plural operators having different values of the foregoing a. For example, by using five reference picture elements t1 to t5, outputs proportional to sizes of foreign matters are obtained from the operators, as shown in FIG. 17(c). In this case, if an identifier indicative of the type of operator detected is attached to the fault output 710, it becomes possible to output the results of detection in a classified manner for each kind of foreign matter. If the coordinate data 703 obtained from the coordinate control/signal control circuit 702 is referenced and added to the inspection output, it is possible to facilitate the work for confirmation and removal after the end of inspection. The data to be added to the inspection output may be the coordinate data 703, or there may be used a coordinate value obtained by correcting the coordinate data 703 using coordinate data in the detection field which is obtained in the decision circuit 708. According to the latter method, it is possible to grasp a detected foreign matter accurately at the time of the work for confirmation or removal.

As set forth above, the transmitted X-ray image signal of the test sample 102 using the point source of X-rays, which is detected from the photoelectric converter 110, is fed to the noise eliminating circuit 704 for the elimination of noise component, then subjected to a logarithmic transformation in the level converter 705 to obtain a transmitted X-ray image signal substantially proportional to the thickness of the test sample, then with respect to this signal, a variation in the inspection area and a variation caused by replacement of the test sample are corrected in the light quantity variation correcting circuit 706 and the shading correction circuit 707, whereby a very small, electroconductive, metallic foreign matter mixed in or adhered to the interior or the test sample such as a prepreg can be inspected at high reliability as the inspection result 112 from the inspection output 710.

The inspection output 710 not only can be outputted to the exterior as the inspection result 112 but also can be utilized again in this apparatus. As shown in FIG. 13, if the XY stage 201 is again moved to the coordinates where a very small, electroconductive, metallic foreign matter is present by the coordinate control/signal control circuit 702 on the basis of the inspection output 710, it is possible to easily effect a visual reconfirmation using X-rays on the monitor 120. In this case, for example, if even a foreign matter detected at a marginal part of the screen is displayed centrally of the screen or a display which indicates a detection site in the form of a circle or an arrow is superimposed on the detection image, using the foregoing coordinate value obtained by correcting the coordinate data 703 using the coordinate data in the detection field, the foreign matter can be identified easily while grasping the entire image of the test sample (object to be inspected).

Figure 18A:
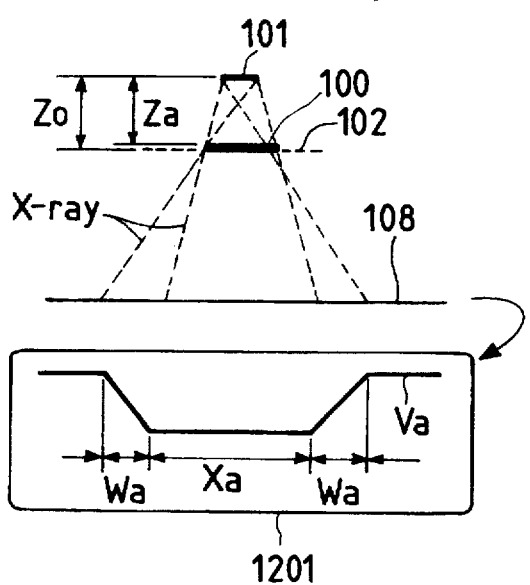
FIGS. 18(a) and 18(b) are diagrams for explaining a decision processing performed in the present invention.
Figure 18B:
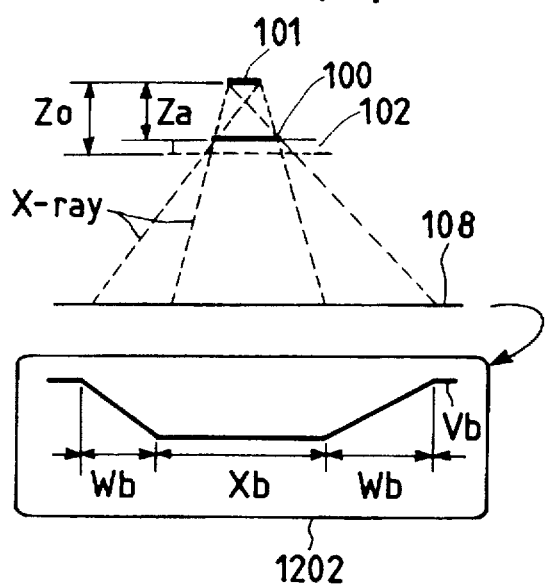

As shown in FIGS. 18(a) and (b), a detected image signal of a foreign matter varies depending on the position in the X-ray radiation direction where the foreign matter is present. If the distance between the X-ray source 101 and the X-ray photoconverter 108 is constant, while there are different distances between the X-ray source 101 and the test sample 102, like Za and Zb, as shown in FIGS. 18(a) and 18(b), images obtained in the X-ray photoconverter 108 are observed as different images in size x, like xa and xb, in detection signals 1201 and 1202 shown in the same figures, or are observed differently in the size w of the waveform rising portion, like wa and wb. Therefore, in the case where the size of the foreign matter 100 in the test sample (object to be inspected) is known in advance, the aforementioned distances Za and Zb in FIG. 18 can be known by measuring the size of x. If the distance ZO between the X-ray source 101 and the stage 201 which carries the test sample 102 thereon is constant, the position in the X-ray radiating direction of the detected foreign matter 100 can be specified from both the foregoing distance z between the x-ray source and the test sample and the distance ZO. Likewise, the position in the X-ray radiating direction of the detected foreign matter can be specified from the value of w. Thus, according to this example, the position in the X-ray radiating direction of the detected foreign matter 100 can be specified, or the size thereof can be estimated from both the said position and the thickness t of the test sample.

In the case where the test sample 102 is a multi-layer printed circuit board or the like, such specific patterns as identification number and alignment mark which are usually provided for each layer can also be used. More specifically, the layer where the foreign matter 100 is present can be determined from the foregoing value of w of the detected foreign matter by checking such specific patterns for each layer, measuring the length wO of the rising portion thereof and making reference to the measured value. According to this example, the layer where the foreign matter is present can be specified even if the position in the X-ray radiating portion of the foregoing stage is unknown.

Figure 19:
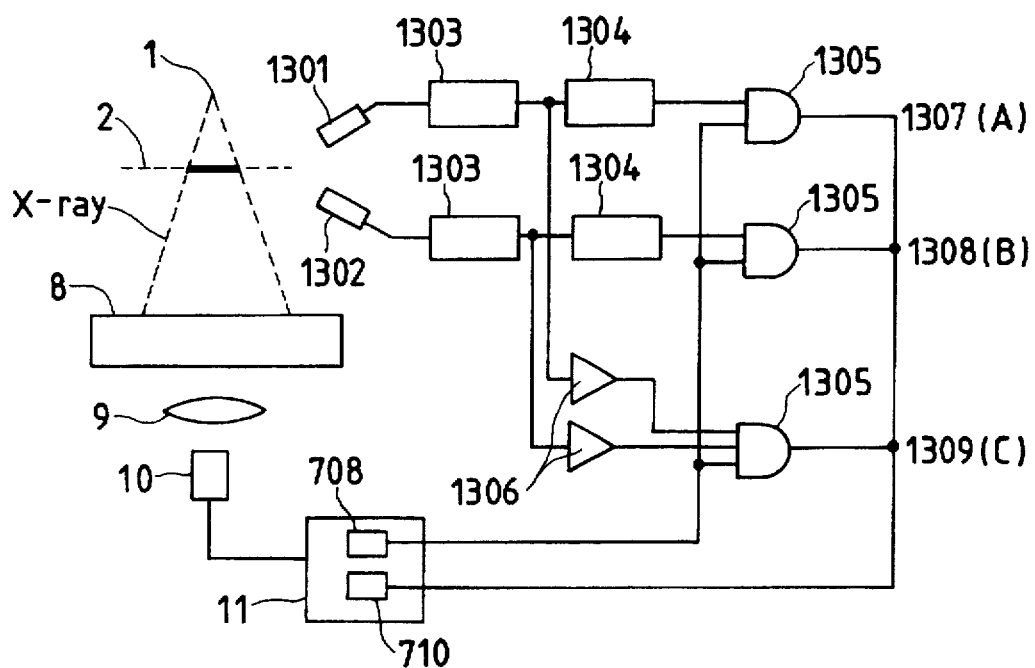
FIG. 19 is an explanatory view showing a further embodiment of the invention wherein a second detection system other than an X-ray system is added to the above inspection apparatus.

By adding a different type of detecting optical system other than one using X-rays to the apparatus as shown in FIGS. 1 or 7, it is also made possible to detect the portion where a very small, electroconductive, metallic foreign matter is present. An example of this construction is illustrated in FIG. 19, in which such detecting optical system is added to only the related portion in FIGS. 1 and 7. In FIG.

19, the numerals 1301 and 1302 each represent a TV camera, which detects the same visual field as that of the photoelectric converter 10 or 110 in interlocked relation with the photoelectric converter. Numeral 1303 denotes a decision circuit such as a binary coding circuit, which extracts an image of the foreign matter from the TV camera 1301 or 1302. Delay circuits 1304 are for synchronizing the detection output 701 with the detection signal. The output of the decision output 708 is ORed with the foreign matter detected by the TV camera 1301 or 1302. As a result, there are obtained outputs (A)1307, (B)1308 and (C)1309. It can be judged that the output (A) indicates the presence of the foreign matter on surface A, output (B) indicates the presence thereof on surface B and output (C) indicates the presence thereof in the interior of the test sample 102. According to this embodiment, such a false information as that which may occur in the foreign matter inspection using only TV cameras is not generated, so the inspection can be done stably. Additionally, the interior of the test sample 102 can also be inspected and it is possible to specify the portion where the foreign matter is present.

Figure 20:
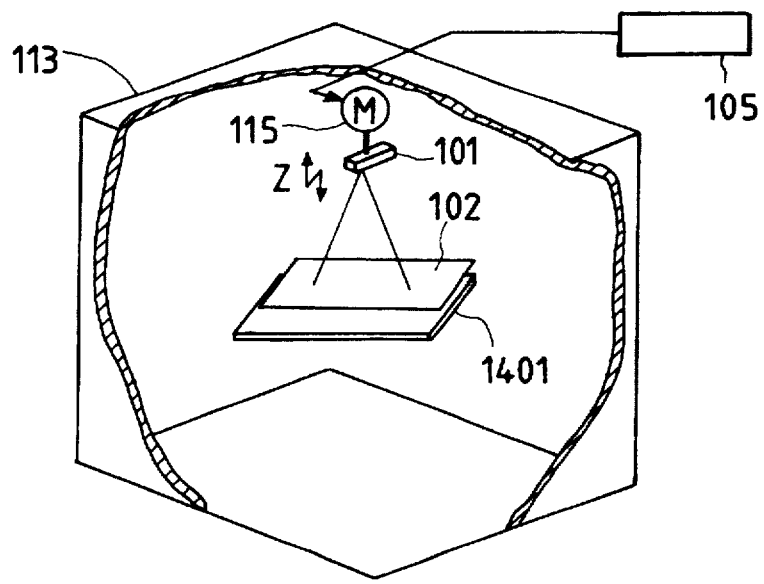
FIG. 20 is a view explanatory of an X-ray apparatus according to a further embodiment of the present invention.
Figure 21:
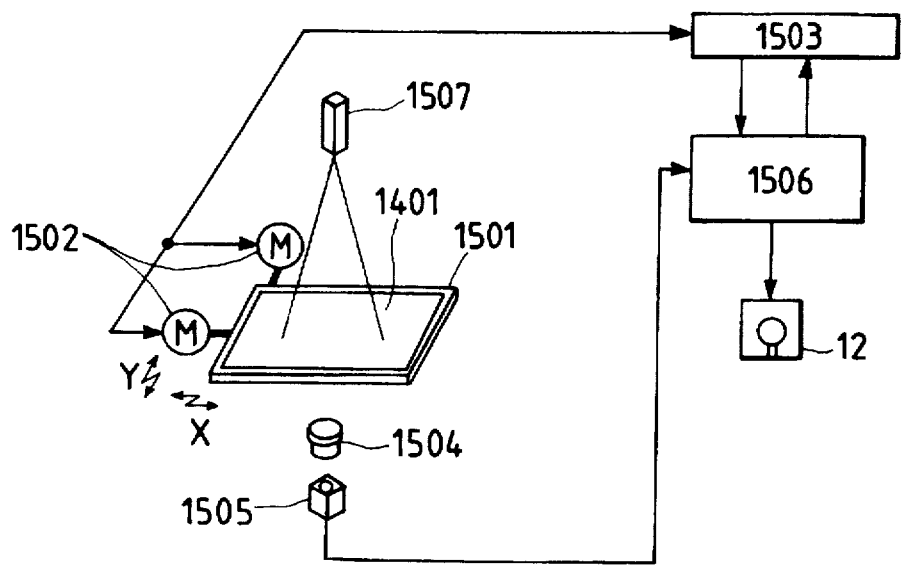
FIG. 21 is a view explanatory of a detection system used together with the X-ray apparatus shown in FIG. 20.

FIGS. 20 and 21 illustrate a further embodiment of the present invention. In FIG. 20, the numerals 101, 102 and 1401 denote an X-ray source, a test sample 102 and a film, respectively, while in FIG. 21, the numeral 1501 denotes an XY positioning stage mechanism, numeral 1502 denotes a motor, numeral 1503 a stage control circuit, numeral 1504 a detecting optical system, numeral 1505 a photoelectric converter, numeral 1506 a signal processing circuit and numeral 1507 a light source. In FIG. 20, a transmitted X-ray image from the test sample 102 is formed on the film 1401. After development, the film 1401 is put onto the positioning stage mechanism 1501, then the light from the light source 1507 is radiated through the film 1401 and the light image developed on the film 1401 is focused by the detecting optical system 1504, then the focused light image is converted to an image signal by the photoelectric converter 1505 and a very small metallic foreign matter is detected in the signal processing circuit 1506. The stage control circuit 1503 and the signal processing circuit 1506 are almost the same as those shown in FIG. 13 which has already been explained. The film 1401 is not specially limited if only the sensitivity to X-rays is satisfied. For example, an imaging plate may be used. Although the transmitting illumination optical system has been described above in connection with FIG. 21, there may be adopted another illumination system, e.g. vertical drop illumination optical system, suitable for the detection medium used such as film or imaging plate. The magnification of the detecting optical system 1504 may be determined suitably so as to permit detection of the foreign matter. According to this embodiment, since imaging for film or the like can be achieved in a short time, it is possible to improve the availability of the expensive X-ray apparatus and thereby reduce the inspection cost.

If a second stage or detection system interlocked with the XY positioning stage mechanism 1501 shown in FIG. 21 is provided in the X-ray apparatus shown in FIG. 20, like FIG. 7, and the test sample 102 is put on the second stage, it is possible to move the test sample 102 in interlocked relation with the inspection and therefore, upon detection of a foreign matter, it is possible to confirm it through the test sample 102 using X-rays.

It is optional whether the X-ray source 101 used in the embodiments of the present invention illustrated in FIGS. 7, 20, etc. is the conventional bremsstrahlung type, or the type in which electron beam or the like is converged to a very small area to generate X-rays, or the type which utilizes synchrotron radiation.

Figure 22A:
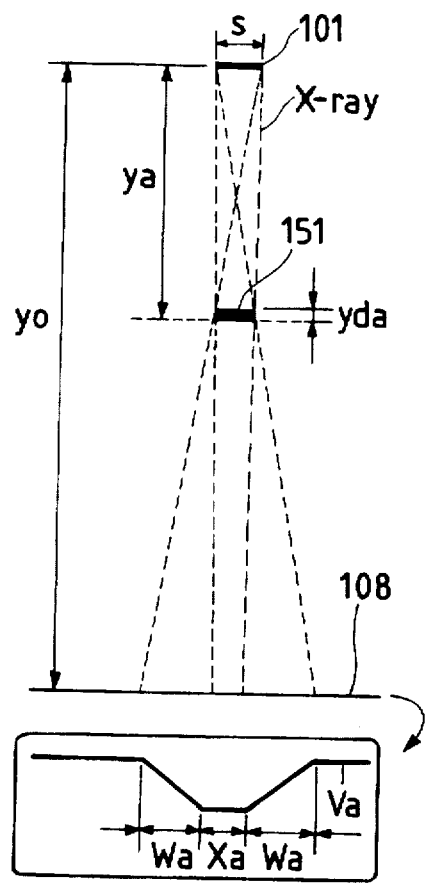
FIGS. 22(a) and 22(b) are explanatory views regarding detection signals in the use of X-rays.
Figure 22B:
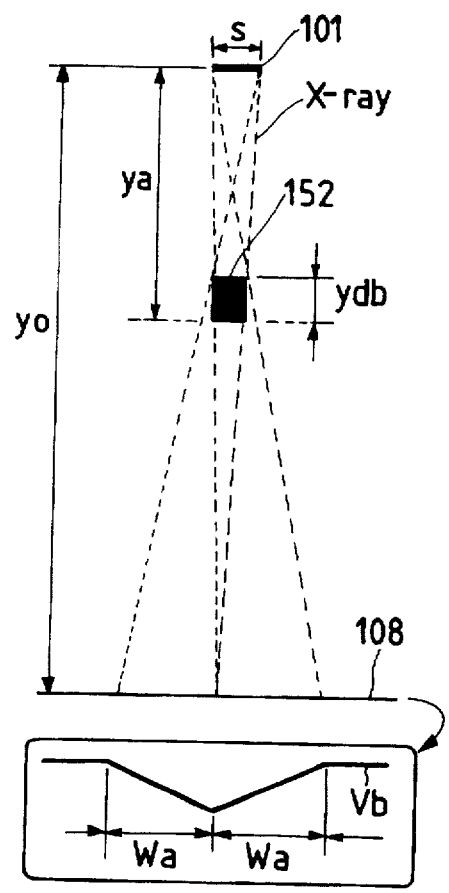
Figure 23:
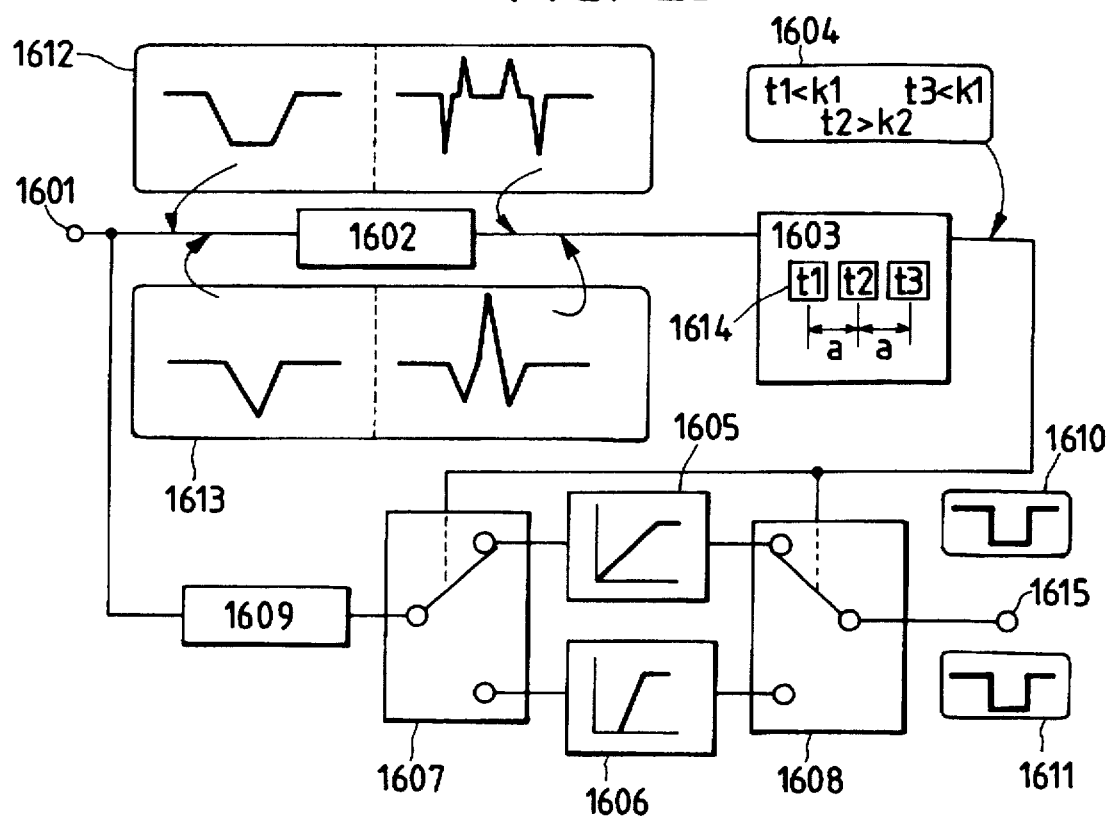
FIG. 23 is an explanatory view showing an example of a signal processing system according to the invention.

Generally, in the case of using X-rays, there occurs such blur w as in FIGS. 22(a) and (b). This depends on the size, s, of the X-ray source 101, distance ya between the X-ray source and the test sample, distance yb between the X-ray source and the X-ray photoconverter, and heights yda, ydb of foreign matters indicated at 151 and 152, respectively. Particularly, when the distance between the X-ray source and the sample relative to the size s, there occurs such a case as FIG. 22(b) in which there is not obtained an area, x, having a density change sufficient for detection. In view of this point, for example by adding such an image processing circuit as shown in FIG. 23 to the input section of the decision circuit 708 in FIG. 13, it is made possible to improve the signal quality. In FIG. 23, an input signal 1601 is applied to a secondary differentiating circuit indicated at 1602. In this case, signal waveforms corresponding to FIG. 22(a) and those corresponding to FIG. 22(b) are as shown in 1612 and 1613, respectively, as waveforms before and after processing. In a feature extraction circuit 1603 there is made decision of the following equation (Equation 7) using k1 and k2 as arbitrary constants by an operator 1614 consisting of reference picture elements t1, t2 and t3 which are arranged at intervals of distance a. When equation 7 is valid, a true control signal 1604 of "1" is outputted, while when equation 7 is not valid, a control signal 1604 of "0" is outputted.

$$t1<k1 \text{ and } t2 >k2 \text{ and } t3<k1 \quad \text{(Equation 7)}$$

The shape of the above operator and values of k1, k2 may be determined from a detection signal obtained in advance. The input signal 1601 is taken in synchronism in a delay circuit 1609, then is switched by switches 1607 and 1608 (switched to the lower side when the output is "1" and to the upper side at "0") and its level is changed by a signal converter 1605 or 1606 constituted by a look-up table, for example. If the signal converters 1605 and 1606 have such input-output characteristics as described in 1605 and 1606 in FIG. 23, the signal waveform indicated at 1612 is changed into that indicated at 1610 and the signal waveform indicated 1613 is changed into that indicated at 1611, which are transmitted as improved signal waveforms to an output 1615. According to this embodiment, even a signal from a foreign matter which is very small and difficult to detect can be detected stably and thus it is possible to improve the detection accuracy.

In the case where an image intensifier (hereinafter referred to simply as "I.I.") is used as the X-ray photoconverter 108 in FIG. 7, a detected image involves a pincushion distortion because the input surface of I.I. is usually spherical. The following description is now provided concerning an example for diminishing such distortion. As well known, if a plano-convex lens is disposed so that the convex surface is on the object side and the plane is on the image surface side, there occurs a barrel distortion. Therefore, the aforementioned pincushion distortion can be cancelled by adding such an optical system as plano-convex lens having a barrel distortion which corrects the pincushion distortion to the detecting optical system 109. On the input side of the I.I., X-rays are converted to electrons and the electrons are converged by the use of an electromagnetic electron lens, while on the output side thereof there is performed an electronic photoconversion. Therefore, the electron lens may be constituted so as to have a barrel distortion. Or a mechanism for generating magnetism which generates a barrel distortion in the electron lens may be provided in the input section of the I.I. to cancel the pincushion distortion.

Figures 24A, 24B:
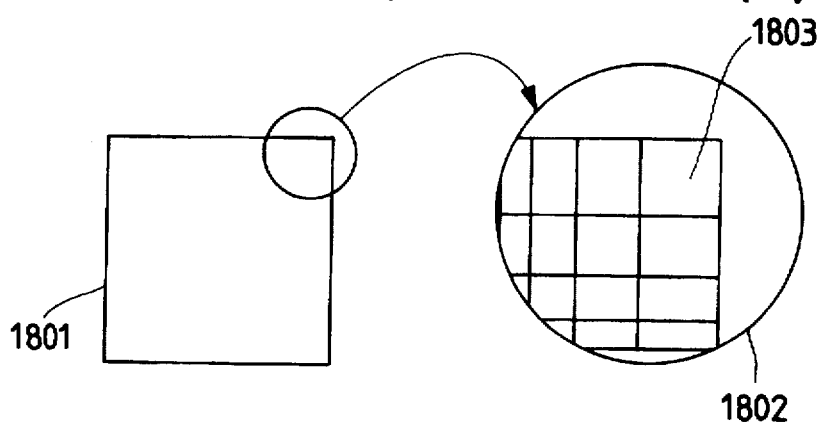
FIG. 24(a) is an explanatory view showing an example of a photoelectric converter according to the invention.
FIG. 24(b) shows an enlarged portion of FIG. 24(a)

According to another example, the picture elements of the photoelectric converter 110 in FIG. 7 are arranged in conformity with the pincushion distortion, whereby the pincushion distortion can be eliminated. In FIG. 24(a), a photoelectric converter 1801 is assumed to be a CCD sensor. Usually, picture elements are arranged in the form of a square lattice, but as shown in FIG. 24(b), using a picture element 1803 in an enlarged view 1802, the picture elements located at the marginal portion are made larger than those at the central portion. If the read-out speed of each picture element is constant, the photoelectric converter 1801 shown in FIG. 24(a) has a barrel distortion. Therefore, if the picture elements 1803 are constituted so as to cancel the pincushion distortion, there eventually can be obtained an image free of distortion.

In the case where the photoelectric converter 110 in FIG. 7 is an image pickup tube, the pincushion distortion can be eliminated by performing the scan of the image pickup tube in a non-linear manner. FIG. 25(a) illustrates an ordinary scanning method. The abscissa in the same figure represents time and the ordinate represents a scanning voltage applied to the image pickup tube. A desired part within the tube surface is subjected to photoelectric conversion by changing the magnitude of the said voltage. In FIG. 25(a), the upper portion represents scanning in the horizontal direction, while the lower portion represents scanning in the vertical direction. Generally, for photoelectric conversion in the form of a square lattice, there is used a saw-tooth waveform wherein the voltage changes linearly with respect to time t. If this is changed into a saw-tooth voltage wherein the time differential of voltage is large at the marginal portion of image, as shown in FIG. 25(b), the image formed has a barrel distortion. Therefore, if the waveform shown in FIG. 25(b) is set so as to cancel the pincushion distortion and photoelectric conversion is performed in the image pickup tube using such waveform, it is possible eventually to obtain an image free from distortion.

Another pincushion distortion eliminating arrangement is shown in FIG. 26, in which the test sample 102 is rested on and along a test sample tray 2001 having a curved surface, whereby the shape thereof is deformed so as to cancel the pincushion distortion. Or in the signal processing circuit 111 shown in FIG. 13, coordinate conversion and level conversion of image may be performed image-processing wise so as to eliminate the pincushion distortion.

In the apparatus using an electromagnetic electron lens such as the X-ray photoconverter 108 described previously, a detected image is deformed under the influence of external magnetic field, etc. In order to enhance the rigidity of the apparatus support structure, an iron frame is used in many cases, but the iron frame is easily magnetized and there occurs the problem that the detected image is deformed under the influence of such magnetism. If the X-ray photoconverter is shielded using a material having a high permeability such as permalloy for example, it is possible to eliminate the influence. On the detector input side, the influence of incoming external magnetic field can be eliminated by disposing a cylindrical member having a high magnetic permeability such as a shield member 2101 shown in FIG. 27. In the case where the magnification of the X-ray photoconverter 108 can be changed by changing the magnification of the above electron lens, it is recommended to provide an input-side diaphragm 2102 formed of a material having a low X-ray transmittance, which is shown in FIG. 27, to eliminate the input of unnecessary X-rays. This is because in the case of increasing magnification, that is, when the part of the input surface of the X-ray photoconverter is projected on the whole output surface, unnecessary X-ray-induced electrons inputted to the outside of the effective input surface are reflected within the X-ray photoconverter 108, reach the output side of the same photoconverter and act like stray light in the optics. According to this embodiment, the deterioration of the detected image caused by the magnetic field outside the X-ray photoconverter 108 or the unnecessary electrons in the same photoconverter can be prevented and hence it is possible to effect an accurate detection. Basically, it is apparent that, in place of the input-side diaphragm 2102, a mechanism for absorbing the aforementioned unnecessary electrons may be provided within the X-ray photoconverter 108.

Although in the above embodiments the inspection of the insulating sheet called a prepreg, indicated at 221 and used in a multi-layer printed circuit board 220 which is fabricated in such a manner as shown in FIG. 28, has been described, it is needless to say that a multi-layer board, ceramic circuit board, display device such as liquid crystal, glass fiber, as well as powder and liquid, can also be inspected and that all of proper objects can be inspected in view of the principle of the inspection.

By fabricating a product such as a circuit board after making inspection using the apparatus of the present invention, it is made possible to eliminate or remedy defects during the fabrication, so the product yield is improved and the reduction of cost can be attained.

In a clean room or the like there usually is laid a dust collecting mat or the like, but if such mat is inspected by the apparatus of this embodiment, it is possible to easily grasp the degree of generation of foreign matter in the clean room or the kind of foreign matter present therein and thus it is possible to control the manufacturing site accurately. It is a matter of course that the same effects can be obtained also with respect to air filters or filters for liquid.

Figure 28A:
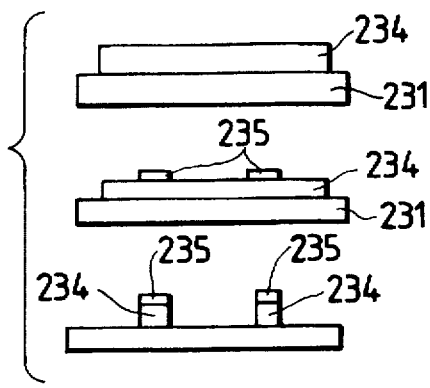
FIGS. 28(a)–28(e) show a view showing a method for fabricating a multi-layer printed circuit board according to the invention.
Figure 28B:
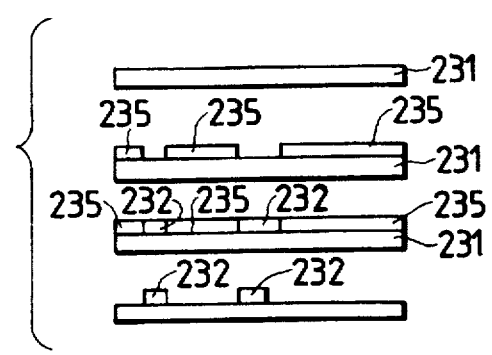
Figure 28C:
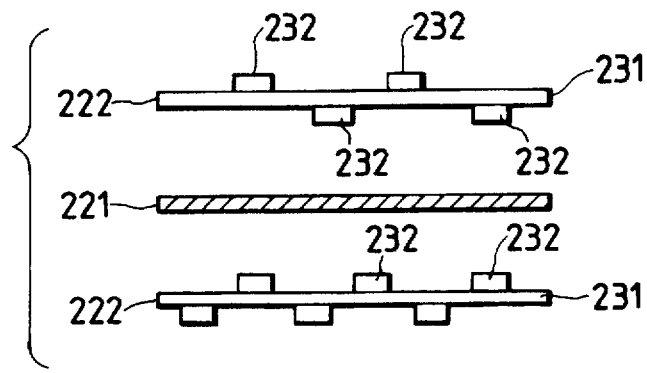
Figure 28D:
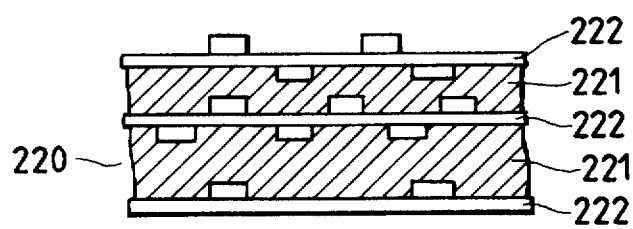
Figure 28E:
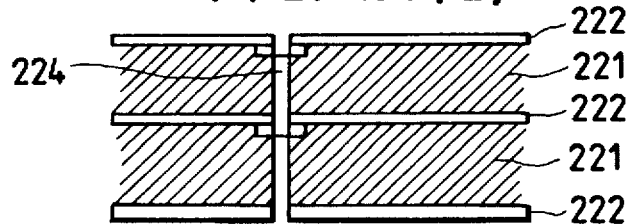

The multi-layer printed circuit board 220 is fabricated in such a manner as shown in FIGS. 28(a)–(e). That is, a resist 235 is applied to an insulating material 231 with wiring material 234 formed thereon and predetermined wiring patterns are formed by exposure and development, followed by etching to remove the resist, to obtain a board 222 having the wiring patterns as shown in FIGS. 28(a) and 28(c). Alternatively, predetermined resist patterns 235 are formed on the insulating material 231 by exposure or printing, followed by plating for the resist patterns 235 to form wiring patterns 232, and thereafter the resist patterns 235 are removed to obtain a board having the wiring patterns. With respect to the board 222 having the wiring patterns thus formed, and an insulating sheet such as a prepreg 221, inspection is made as to whether a very small, electroconductive, metallic foreign matter is present or not on the surface or in the interior, using the X-ray inspection apparatus described above. On the basis of this inspection there are provided such boards and insulating sheets not containing the said foreign matter in an amount exceeding a predetermined value. The boards 222 and insulating sheets 221 thus provided are laminated, heated and pressurized to afford a laminated multilayer printed circuit board as shown in FIG. 28(d). Thereafter, through holes 224 are formed where required and the interior is placed for connection between layers as shown in FIG. 28(a). By subsequent mounting of electronic parts on the surface of the multi-layer printed circuit board, there is obtained a product.

Such a multi-layer printed circuit board used in the fabrication of an electric circuitry is manufactured by impregnating mesh-like woven fabric sheet of glass fiber with an insulating material such as polyimide to afford an insulating sheet called a prepreg, then forming wiring patterns (circuit patterns) on the surface of the insulating sheet, using an electrically conductive material such as copper, to obtain a wiring pattern board 222 and laminating a large number of such boards through the insulating sheet 221 called a prepreg. However, if an electroconductive metallic foreign matter is mixed in or adhered to the interior or the surface of the insulating sheet 221, the wiring patterns 232 will be short-circuited or assume a state akin to short-circuit, so it is necessary to check this point and eliminate defects if any. For ensuring reliability over a long period after the fabrication of the multi-layer printed circuit board, even if such electroconductive metallic foreign matter measures not larger than several ten μm, it is necessary to detect it to prevent the deterioration of insulation characteristics caused by migration for example of the wiring patterns formed of copper for example. In view of this point, the insulating sheet 221 called a prepreg and used in the invention is constituted by a material of a relatively low molecular weight and high X-ray transmittance, while the metal such as Fe, Mo or W causing problem as an electroconductive metallic foreign matter is high in molecular weight and relatively low in X-ray transmittance. Taking note of this point, the present invention provides that a very small, electroconductive metallic foreign matter mixed in or adhered to the interior or the surface of the insulating sheet called a prepreg can be inspected at high reliability on the basis of a transmitted X-ray image. Consequently, such foreign matter is present in the interior or on the surface of the insulating sheet 221 only in an amount not larger than a predetermined value, so if a multi-layer printed circuit board is fabricated by laminating a large number of the wiring pattern boards 222 through the insulating sheet 221 free of the foregoing very io small, electroconductive, metallic foreign matter, the multi-layer printed circuit board can be ensured its insulation characteristics and reliability over a long period.

According to the present invention, a clear transmitted X-ray image can be obtained from an object to be inspected. Consequently, if the object to be inspected is assumed to be a printed circuit board, then by inspecting a clear image corresponding to the circuit pattern portion, it is made possible to detect even a fine defect (e.q. short or excess thickness) present on a circuit pattern, typified by disconnection, whereby the reliability of the printed circuit board can be improved. Further, since a very small, electroconductive, metallic foreign matter mixed in or adhered to the interior or the surface of an insulating sheet called a prepreg and used in the fabrication of a multi-layer printed circuit board or the like can be inspected at high reliability on the basis of a transmitted x-ray image, it is possible to ensure high insulation characteristics and reliability over a long period.

We claim:

1. An X-ray inspection method comprising the steps of:
    generating from a target characteristic X-rays which differ from continuous X-rays generating Bremsstrahlung radiation, the characteristic X-rays containing at least one wavelength having a peak level which affords a high X-ray absorbance in an object to be inspected;
    irradiating the object to be inspected with the characteristic X-rays;
    detecting a transmitted X-ray image which has passed through the object to be inspected; and
    inspecting the object to be inspected on the basis of the transmitted X-ray image.

2. An X-ray inspection method according to claim 1, wherein the step of radiating includes radiating to the object to be inspected characteristic X-rays containing at least two wavelengths which afford a high X-ray absorbance in the object to be inspected.

3. An X-ray inspection method according to claim 1, wherein the object to be inspected is a printed circuit board having wiring patterns, the step of radiating includes radiating to the printed circuit board characteristic X-rays containing at least one wavelength of 0.04 to 0.15 nm which affords a high X-ray absorbance in the wiring patterns on the printed circuit board, the step of detecting includes detecting a transmitted X-ray image which has passed through the printed circuit board, and the step of inspection includes inspecting the printed circuit board on the basis of said transmitted X-ray image.

4. An X-ray inspection method according to claim 3, wherein the printed circuit board has wiring patterns of Cu or Au.

5. An X-ray inspection method according to claim 3, wherein the printed circuit board has wiring patterns of Cr or Au.

6. An X-ray inspection method according to claim 5, wherein the step of radiating includes radiating to the printed circuit board having wiring patterns of Cr or Au characteristic X-rays containing at least one wavelength of 0.04 nm to 0.15 nm and generated by radiating a converged electron beam to a target formed of Mo, Cu or Au, or an alloy thereof.

7. An X-ray inspection method according to claim 6, wherein the step of radiating includes radiating to a printed circuit board having wiring patterns of Cr or Au characteristic X-rays containing at least one wavelength of 0.04 nm to 0.15 nm and generated from a very small area of the target having a dimension or 20 μm or less by radiating the converged electron beam to the small area of the target, the target being formed of Mo, Cu or Au, or an alloy thereof.

8. An X-ray inspection method according to claim 1, wherein the object to be inspected is an insulating member, the step of radiating includes radiating to the insulating member characteristic X-rays containing at least one wavelength of 0.04 nm to 0.15 nm and generated by radiating a converged electron beam to a target formed of Mo, Cu or Au, or an alloy thereof, the step of detecting includes detecting a transmitted X-ray image which has passed through insulating member, and the step of inspecting includes inspecting a fine, electroconductive, metallic foreign matter present on the surface or in the interior of the insulating member on the basis of the transmitted X-ray image.

9. An X-ray inspection method according to claim 8, wherein the step of radiating includes radiating to the insulating member characteristic X-rays containing at least one wavelength of 0.04 nm to 0.15 nm and generated from a very small area of the target having a dimension of 20 μm or less by radiating the converged electron beam to the small area of the target.

10. An X-ray inspection method according to claim 1, wherein the object to be inspected is a prepreg.

11. A method according to claim 1, wherein:
    the step of radiating includes radiating X-rays to a prepreg as the object to be inspected; and
    the steps of detecting and inspecting include checking whether a specified electroconductive foreign matter is mixed in the interior of the prepreg or adhered to the surface of the prepreg on the basis of a transmitted X-ray light/shade image which has passed through the at least one prepreg.

12. A method according to claim 11, wherein the at least one prepreg is disposed in a bag and the X-rays are radiated through the bag.

13. A method according to claim 11, further comprising the steps of:

providing a prepreg free of the specified electroconductive foreign matter mixed in or adhered to the interior or the surface of the prepreg; and laminating and heating the provided prepreg and a printed circuit board having wiring patterns on an insulating material to fabricate a multi-layer printed circuit board.

14. A method according to claim 13, further comprising the steps of extracting only the portion where the wiring patterns are present on the printed circuit board on the basis of a design information of the printed circuit board which is in contact with a prepreg, and inspecting only the extracted portion of the prepreg or the printed circuit board to eliminate defects.

15. An X-ray inspection method according to claim 1, wherein the characteristic X-rays generated from the target pass through a filter before the characteristic X-rays radiated the object to be inspected.

16. An X-ray inspection method according to claim 15, wherein the filter cuts off an X-ray of a wavelength affording a low X-ray absorbance in the object to be inspected.

17. An X-ray inspection apparatus comprising:

an X-ray target for generating characteristic X-rays which differ from continuous X-rays generating Bremsstrahlung radiation, the characteristic X-rays containing at least one wavelength having a peak level which affords a high X-ray absorbance in an object to be inspected;

means for radiating the characteristic X-rays to the object to be inspected;

means for detecting a transmitted X-ray image which has passed through the object; and means for inspecting the object to be inspected on the basis of the transmitted X-ray image.

18. An X-ray inspection apparatus according to claim 17, further comprising a stage for resting the object to be inspected thereon and for positioning the object, and a stage controller for controlling the movement of the stage, the X-ray source radiating X-rays to the object to be inspected which has been positioned by the stage, the means for detecting including an optical image converter for detecting and converting a transmitted X-ray image which is passed through the object into an optical image and a photoelectric converter for converting the optical image obtained by the optical image converter into a transmitted X-ray image signal, the means for inspecting including an image processor for inspecting the object to be inspected on the basis of the transmitted X-ray image signal obtained by the photoelectric converter.

19. An X-ray inspection apparatus according to claim 18, wherein the X-ray source radiates X-rays containing a plurality of wavelengths which afford a high X-ray absorbance in the object to be inspected.

20. An X-ray inspection apparatus according to claim 19, wherein the X-ray source is constituted by an X-ray tube having a controllable tube voltage and a controllable tube current.

21. An X-ray inspection apparatus according to claim 20, wherein the X-ray tube has a target formed of the same material as that of the object to be inspected.

22. An X-ray inspection apparatus according to claim 20, wherein the X-ray tube has a target formed of an alloy of two or more kinds of metals.

23. An X-ray inspection apparatus according to claim 17, wherein the object to be inspected is a test sample, the X-ray source being an X-ray source for radiating X-rays to the test sample in X and Y axis directions; the means for detecting including an X-ray photoconverter for detecting and converting a transmitted X-ray image which has passed through the test sample positioned by an XY positioning stage into an optical image; a photoelectric converter for receiving and converting the optical image detected by the X-ray photoconverter as a transmitted light/shade X-ray image signal; a noise eliminating unit for eliminating a noise component from the transmitted light/shade image signal obtained by the photoelectric converter; at least one level conversion unit for converting the level of the transmitted light/shade X-ray image signal after noise elimination by the noise eliminating unit into a signal level proportional to the thickness of the test sample; and a level correction unit for correcting a change in a detected signal level of the transmitted light/shade image signal after conversion by the level conversion unit; and the means for inspecting inspects foreign matter mixed into the test sample and foreign matter adhered to the surface of the test sample on the basis of the transmitted light/shade X-ray image signal after correction by the level correction unit.

24. An X-ray inspection apparatus according to claim 23, wherein the X-ray source is constructed so as to radiate an electron beam convergedly in a very small area of a target and to cause X-rays to be generated from the very small area of the target so as to be radiated therefrom.

25. An X-ray inspection apparatus according to claim 23, further including an imaging magnification controller for controlling an imaging magnification of the transmitted X-ray image detected by the X-ray photoconverter.

26. An X-ray inspection apparatus according to claim 23, further including a conveyor for carrying the test sample as a test sample tray in and out between an auxiliary stage disposed outside a protective cabinet and the XY positioning stage through a window having an opened and closed position and formed in the protective cabinet.

27. An X-ray inspection apparatus according to claim 23, further including an X-ray measuring unit for measuring the intensity of X-rays emitted from the X-ray source, and wherein the detected signal level is corrected by the level correction unit in accordance with the intensity of X-rays measured by the X-ray measuring unit.

28. An X-ray inspection apparatus according to claim 23, further including an X-ray measuring unit for measuring the intensity of X-rays emitted from the X-ray source, and a controller for controlling the X-rays emitted from the X-ray source in accordance with the intensity of X-rays measured by the X-ray measuring unit.

29. An X-ray inspection apparatus according to claim 23, further including a display unit for displaying the transmitted light/shade X-ray image signal after correction by the level correction unit.

30. An X-ray inspection apparatus according to claim 23, further including at least one non-X-ray detection unit wherein positions of the detected foreign matter are distinguished in accordance with the result of detection by the at least one non-X-ray detection unit on the basis of coordinates detected using X-rays.

31. An X-ray inspection apparatus according to claim 30, further including a signal processing circuit for detecting a degree of a change in a detection signal contained in the transmitted X-ray image, and wherein the kind of each foreign matter is classified on the basis of the degree of the change, and further in combination with the result of detection corresponding to a coordinate position and obtained by the at least one non-X-ray detection unit, and the result obtained is outputted.

32. An X-ray inspection apparatus according to claim 23, wherein the photoelectric converter comprises a detecting optical system and a photoelectric converter device, the detecting optical system being constructed so as to correct a distortion generated in the X-ray photoconverter.

33. An X-ray inspection apparatus according to claim 32, wherein a read scan signal is provided for the photoelectric converter device so as to correct distortion generated in the X-ray photoconverter.

34. An X-ray inspection apparatus according to claim 23, wherein the photoelectric converter has a plurality of picture elements and that picture elements are larger in size at a marginal portion of a detection field than at a central portion of the detection field.

35. An X-ray inspection apparatus according to claim 23, further including a mechanism for switching one of a plurality of level conversion units from one to another among the plurality of level conversion units, and a mechanism for making the corrected value from the at least one level correction unit rewritable, whereby a change in detection sensitivity caused by one of a change in sensitivity characteristic of the X-ray photoconverter or by a change in the type of the test sample is corrected into a predetermined reference characteristic.

36. An X-ray inspection apparatus according to claim 23, further including a signal processing circuit for detecting a degrees of a change in a detection signal contained in the transmitted X-ray image, and wherein the position of each foreign matter is distinguished on the basis of the degree of the change.

37. An X-ray inspection apparatus according to claim 23, wherein the test sample includes a test sample tray for X-rays having a test sample holding portion formed of a material low in X-ray transmittance, and a frame portion which supports only the peripheral part of the holding portion so as not to be an obstacle to detection.

38. An X-ray inspection apparatus according to claim 37, wherein the test sample tray has a shape which causes the test sample to be distorted convexly to correct a pincushion distortion generated in an X-ray photoconverter.

39. An X-ray inspection apparatus according to claim 23, further comprising a standard sample which has been made clear with respect to the amount of X-rays passing therethrough, the amount of X-rays passing through the standard sample being detected before the start of inspection of a test sample to obtain a reference value of a detected signal level, and on the basis of the reference value, the detected signal level is corrected by the at least one level correction unit, or X-rays emitted from an X-ray source are controlled by an X-ray controller.

40. An X-ray inspection apparatus according to claim 23, wherein an X-ray passage is formed in a frame portion, a standard sample which has been made clear with respect to the amount of X-rays passing therethrough is placed on the passage, the amount of X-rays passing through said standard sample being detected before the start of inspection of a test sample to obtain a reference value of a detected signal level, and on the basis of the reference value, the detected signal level is corrected by the at least one level correction unit, or X-rays emitted from an X-ray source are controlled by an X-ray controller.

41. A system including an inspection apparatus according to claim 17, for controlling the state of generation of dust, comprising one of dust collecting filters and adhesive sheets disposed in positions within the inspection apparatus, and transmitting X-rays for inspection of the state of generation of dust.

42. An X-ray inspection apparatus according to claim 17, further including:

an auxiliary stage disposed outside of a protective cabinet;

an XY positioning stage for moving and positioning a test sample in X and Y axis directions;

a conveyor for carrying the test sample in and out between the auxiliary stage and the XY positioning stage through a window having an opened and closed position and formed in the protective cabinet;

the X-ray source being constructed so as to radiate an electron beam convergedly to a very small area of a target and to cause X-rays to be generated from the very small area of the target;

the detecting means including a sensitizing unit for picking up and sensitizing a transmitted X-ray image which has passed through the test sample irradiated with X-rays from said X-ray source and positioned by the XY positioning stage onto a film so as to obtain an X-ray transmitted image; and the inspecting means inspecting foreign matter mixed into the test sample and a foreign matter adhered to the surface of the test sample after detection by the sensitizing unit.

43. An X-ray inspection apparatus according to claim 17, wherein the means for radiating includes a filter located between the target and the objected to be inspected.

44. An X-ray inspection apparatus according to claim 43, wherein the filter cuts off an X-ray of a wavelength affording a low X-ray absorbance in the object to be inspected.

45. An X-ray inspection method comprising the steps of:

irradiating an electron beam to a target which contains at least one element of Mo, Cu and Au;

generating characteristic X-rays from the target which contain at least one wavelength having a peak level between 0.04 and 0.15 nm in relation to an object to be inspected;

radiating the characteristic X-rays to a printed circuit board having-wiring patterns of Cu or Au as the object to be inspected;

detecting a transmitted X-ray image which has passed through the object to be inspected; and inspecting the object to be inspected on the basis of the transmitted X-ray image.

46. An X-ray inspection apparatus comprising:

an X-ray tube which generates characteristic X-rays from a target containing at least one element of Mo, Cu and Au, the characteristic X-rays containing at least one wavelength having a peak level between 0.04 and 0.15 nm in relation to an object to be inspected, and which irradiates the characteristic X-rays generated from the target to the object to be inspected;

a detector which detects a transmitted X-ray image which has passed through the object to be inspected; and means for inspecting the object to be inspected on the basis of the transmitted X-ray image.

* * * * *